(12) United States Patent
Cao et al.

(10) Patent No.: US 10,743,826 B2
(45) Date of Patent: Aug. 18, 2020

(54) STATIONARY REAL TIME CT IMAGING SYSTEM AND METHOD THEREOF

(71) Applicant: NANOVISION TECHNOLOGY (BEIJING) CO., LTD., Beijing (CN)

(72) Inventors: Hongguang Cao, Beijing (CN); Yunxiang Li, Beijing (CN); Tong Chang, Beijing (CN); Zhili Cui, Beijing (CN); Hailiang Zheng, Beijing (CN)

(73) Assignee: NANOVISION TECHNOLOGY (BEIJING) CO., LTD., Beijing (CN)

(*) Notice: Subject to any disclaimer, the term of this patent is extended or adjusted under 35 U.S.C. 154(b) by 683 days.

(21) Appl. No.: 15/443,985

(22) Filed: Feb. 27, 2017

(65) Prior Publication Data
US 2017/0164910 A1 Jun. 15, 2017

Related U.S. Application Data

(63) Continuation of application No. PCT/CN2015/088067, filed on Aug. 25, 2015.

(30) Foreign Application Priority Data

Aug. 26, 2014 (CN) .......................... 2014 1 04250612

(51) Int. Cl.
*A61B 6/00* (2006.01)
*G01T 1/29* (2006.01)
(Continued)

(52) U.S. Cl.
CPC .......... *A61B 6/4014* (2013.01); *A61B 6/4007* (2013.01); *A61B 6/4241* (2013.01);
(Continued)

(58) Field of Classification Search
CPC ... A61B 6/4007; A61B 6/4014; A61B 6/4021; A61B 6/405; A61B 6/4064; A61B 6/42;
(Continued)

(56) References Cited

U.S. PATENT DOCUMENTS 7,706,499 B2* 4/2010 Pack ...................... A61B 6/027
378/10
7,835,486 B2 11/2010 Basu et al.
(Continued)

FOREIGN PATENT DOCUMENTS

CN 101512380 8/2009
CN 102697518 10/2012
(Continued)

OTHER PUBLICATIONS

Dr. Jeffrey Hesler, "From GHZ to THz: The Essentials of Very High Frequency Signal Measurements" (2012), Virginia Diodes, Inc., and Agilent Technologies, at https://www.keysight.com/upload/cmc_upload/All/WS5_Monday_14.15_Jeffrey_Hesler.pdf (Year: 2012).*

*Primary Examiner* — Anastasia Midkiff
(74) *Attorney, Agent, or Firm* — Muncy, Geissler, Olds & Lowe, P.C.

(57) ABSTRACT

The present invention discloses a stationary real-time CT imaging system, comprising an annular photon counting detector, an annular scanning x-ray source, and a scanning sequence controller. Under the control of the scanning sequence controller, the annular scanning x-ray source emits x-ray, and the x-ray penetrates the object being tested and projects onto the corresponding annular photon counting detector. The annular photon counting detector delivers the corresponding exposure information through the main scanning machine and the main controlling unit to a CT main machine and a human-machine interface unit. The image reconstruction is completed in the CT main machine and the human-machine interface unit. By electronically controlling (Continued)

and switching x-ray projection positions in order, the scanning speed is enhanced by tens of times, thereby obtaining dynamic 3D images. The use of the photon counting detector enables the access to absorption data and energy data, thereby allows for real-time data reconstruction.

11 Claims, 25 Drawing Sheets

(51) Int. Cl.
    *H05G 1/70* (2006.01)
    *H05G 1/46* (2006.01)
    *G01N 23/10* (2018.01)
(52) U.S. Cl.
    CPC .......... *A61B 6/4266* (2013.01); *A61B 6/4275* (2013.01); *G01T 1/29* (2013.01); *H05G 1/70* (2013.01); *A61B 6/486* (2013.01); *G01N 23/10* (2013.01); *H05G 1/46* (2013.01)
(58) Field of Classification Search
    CPC ... A61B 6/4208; A61B 6/4241; A61B 6/4266; A61B 6/4275; A61B 6/44; A61B 6/4429; A61B 6/4435; A61B 6/4447; A61B 6/48; A61B 6/482; A61B 6/54; G01N 23/087; G01N 23/10; G01N 23/20091; G01N 2223/206; H05G 1/32; H05G 1/46; H05G 1/56; H05G 1/70; G01T 1/16; G01T 1/29
    See application file for complete search history.

(56) References Cited

U.S. PATENT DOCUMENTS

| | | | |
|---|---|---|---|
| 7,876,881 B2* | 1/2011 | Jeffery | A61B 6/032 378/10 |
| 2007/0003004 A1 | 1/2007 | Delgado et al. | |
| 2008/0265167 A1 | 10/2008 | Laurence et al. | |
| 2012/0300897 A1 | 11/2012 | Flohr et al. | |
| 2013/0251097 A1* | 9/2013 | Zou | A61B 6/032 378/9 |
| 2014/0270054 A1* | 9/2014 | Sampayan | G01N 23/046 378/9 |
| 2016/0151028 A1 | 6/2016 | Liang et al. | |

FOREIGN PATENT DOCUMENTS

| | | |
|---|---|---|
| CN | 102793554 | 11/2012 |
| CN | 203178216 | 9/2013 |
| CN | 103961129 | 8/2014 |

\* cited by examiner

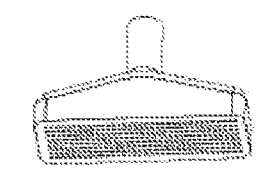
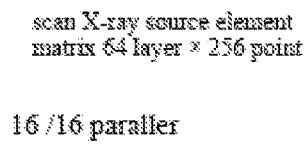
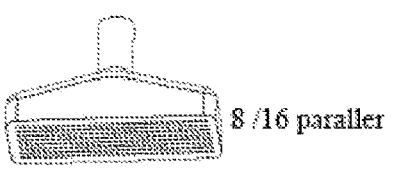
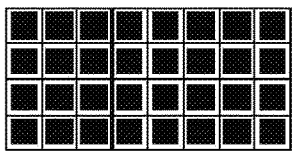
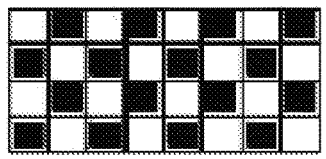
FIG.21A
FIG.21B
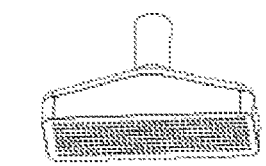
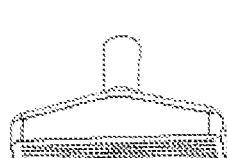
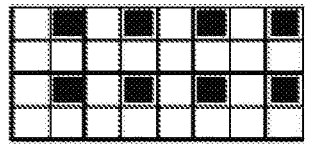
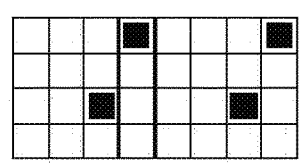
FIG.21C
FIG.21D

STATIONARY REAL TIME CT IMAGING SYSTEM AND METHOD THEREOF

CROSS REFERENCE TO RELATED APPLICATION

This application is a continuation of International Application No. PCT/CN2015/088067, filed on Aug. 25, 2015, which claims priority to Chinese patent application No. 201410425061.2, filed on Aug. 26, 2014, the content of which are incorporated herein by reference in their entirety.

FIELD OF THE INVENTION

The present invention relates to a CT imaging system, particularly to a stationary real time CT imaging system using an annular scanning x-ray source and an annular photon counting detector, and also relates to a real-time CT imaging method based on the CT imaging system, belonging to a field of medical imaging technology.

BACKGROUND OF THE INVENTION

CT (Computed Tomography) is the abbreviation of computer tomography technology. Its imaging principle is as follows: using x-ray beam and x-ray detector of high sensitivity, a part of one person is scanned around by serial slices tomography, the x-ray penetrating the slice of the person is received by scintillator in the x-ray detector, after being converted to visible light, is converted to electric signals by photoelectric conversion device, and is then amplified and converted to digital signals by A/D conversion so as to be processed by a computer. In the computer, the selected slice is divided into a number of boxes of same volume, called a voxel. Information from the serial slices tomography is calculated to get x-ray attenuation coefficients for each voxel, or absorption coefficient for each voxel, which are then arranged in a matrix, i.e. voxel digital matrix. Digital information in the voxel digital matrix is converted to blocks with different grays from black to white, which are known as pixels in two-dimensional projection (Pixel), and the blocks are arranged according to a segment mode to constitute a CT image.

Existing medical CT imaging system was launched in 1972, its inventor won the Nobel Prize. In more than 40 years of application practice, CT technology constantly develops and upgrades (details are shown in FIG. 1, wherein A stands for a first generation CT, B for a second generation CT, C for a third generation CT using a fan beam detector and ray source mechanical rotation, D for a fourth generation CT with an x-ray ball tube and a mechanical rotating generator, E for a fifth generation CT of electron beam rotating, and F for a stationary real-time CT imaging system illustrated as the present invention that uses pencil beam (also known as narrow beam) x-ray sequentially emitting in parallel. For example, early CT imaging system consisting of single-photon-counting detectors and narrow-beam source scans in parallel in varied angles with parallel beams to get data for reconstruction, and then reconstructs three dimensional data through reconstruction algorithm such as Radon Transform. However, such a CT imaging system has low utilization of x-ray, long scan time, poor reconstruction image quality. Later, fan beam CT imaging system with rotation scan is launched. As shown in FIG. 2, the fan-beam CT imaging system includes a plurality of x-ray detectors arranged in an arc and a plurality of x-ray sources with big fan-angle divergent, can envelope a full slice of a person in one time, through a 360-degree scan, to complete one slice image reconstruction, thereby greatly speeding up the imaging process. In recent years, a cone-beam CT imaging system appears. The cone-beam CT imaging system uses detectors in plane array instead of those in linear array, using cone-beam scanning instead of fan-beam scanning, so that x-ray utility becomes more efficient, scanning time turns to be shorter, uniform in all directions and high precision spatial resolution are achieved. However, cone-beam CT imaging system has serious imaging scattering. Therefore, smaller pixels hardly bring fan-beam CT imaging system the same signal to noise ratio, which is the main bottleneck to improve image quality. So, the fan-beam CT imaging system applies mainly at present in small parts of the body.

As x-ray detector continues to be improved, multi-array CT detector including a plurality of x-ray units in a larger fan-angle, can collect 64-row-320-row and even more data in one rotation. In order to get more absorption characteristics of a body, the CT imaging system using multiple-energy x-ray sources to obtain body tissues' x-ray absorption data so as to obtain CT images with energy calibration. However, the existing CT imaging system for imaging still fast enough, there are motion artifacts and other issues. In clinical work, for example, a full heart image reconstructed in a rotation cycle requires CT rotation speeds up to 2 circles per second or even faster. Unfortunately, x-ray sources and x-ray detectors set at high speed rotating frame rotating 2 circles per second or even faster, cause x-ray source, high voltage generators and other assembles to work under the centrifugal force, therefore it turns to be a manufacturing technology bottleneck.

According to Chinese patent application No. CN102793554A, Siemens Company proposes a dual-source CT system having two detectors located in angles staggered from each other. In the dual-source CT system, one detector has a set of integral detector units, and the other detector has a set of counting detector units. On one hand, referring to FIGS. 3A and 3B, at the time of measuring x-ray intensity, integration of amplified electric signals is taken as signal data at this angle. The electric signals are received time intervals during which the detectors rapidly rotate a slight displacement. Because detector pixels signals are integration of the electric signals during a slight displacement, the spatial resolution encounters a bottleneck in a state of high speed rotation, and becomes conflict with rotation speed. The faster the rotation is, the greater the displacement of the pixels in unit time. Thus, signals at different locations crosstalk and overlap (that is, motion trail) more severely. The other hand, the detector has more and more layers, x-ray beams from a x-ray source are wider and wider, x-ray scattering is more and more serious, resulting in the CT images become blurred. In addition, dual-source CT system causes bodies exposed to x-ray two times or exposed to double amount x-ray at one time. Consequently, radiation exposure becomes higher and higher to go far beyond the maximum safe dose for one year.

In addition, the x-ray detectors used in the conventional technologies and those used in the fan-beam multi-slice spiral CT work in an energy integral model. This kind of x-ray detectors cannot distinguish between each x photon spectrum, thus losing energy spectrum information. But, the energy spectrum information is especially important for clinical image interpretation.

SUMMARY OF THE INVENTION

The first objective of the present invention is to provide a stationary real time CT imaging system to overcome the shortage of the traditional technology.

The second objective of the present invention is to provide an imaging method based on the present CT imaging system.

According to the first aspect of the invention, there is provided a stationary real-time CT imaging system, including a bed control unit, a CT host and interface unit, a power control unit, a main processor, and a scan host, wherein:

the scan host includes an annular scanning x-ray source and an annular photon-counting detector parallel to each other;

the annular scanning x-ray source includes a plurality of scanning x-ray sources closely arrayed in a ring, the annular photon-counting detector includes a plurality of photon-counting detector modules closely arrayed in a ring;

the scanning x-ray source sequentially emits narrow beam x-ray, directing to corresponding photon counting detector module, penetrating through an objects, the photon counting detector modules send corresponding exposure information into CT host and interface unit via the scan host and the main processor, the CT host and interface unit completes real time reconstruction of an image and visual reproduction.

Preferably, the main processor has a scan timing controller, which controls a plurality of scanning x-ray sources in different areas to work simultaneously or sequentially.

Preferably, the scanning x-ray source, controlled by the scanning sequence controller, emits narrow beam x-rays point by point, every other point, line by line or every other line.

Preferably, the photon-counting detector module includes a plurality of photon-counting detector units;

the photon-counting detector unit includes a plurality of photon-counting detectors arranged in a rectangle array and connected to a multi-channel photon counting detector acquisition circuit of the scan host through a leader line.

According to the second aspect of the invention, there is provided a stationary real-time CT imaging system, including a bed control unit, a CT host and interface unit, a power control unit, a main processor, and a scan host, wherein:

the scan host includes a multi-focus annular scanning x-ray sources and an annular photon-counting detector;

the multi-focus annular x-ray sources includes a plurality of scanning x-ray sources closely arrayed in a ring, the annular photon-counting detector includes a plurality of photon-counting detector modules closely arrayed in a ring;

the scanning x-ray source sequentially emits fan beam x-ray directing to corresponding photon counting detector module, penetrating through an objects, the photon counting detector modules work with overlap and send corresponding exposure information into the CT host and interface unit via the scan host and the main processor, the CT host and interface unit completes real time reconstruction and visual reproduction of an image.

According to the third aspect of the invention, there is provided a stationary real-time CT Imaging control method realized by the stationary real-time CT imaging system, comprising the following steps:

the scan timing controller controls the photon-counting detector modules at different spatial positions and corresponding narrow-beam x-ray source to work in different scan timing;

the scanning x-ray source emits narrow beam of x-rays in accordance with a preset emission timing, and the corresponding photon-counting detector module collects exposure information of the narrow beam x-rays passing through objects to the photon-counting detector module.

In comparison with the traditional technology, the present invention provides the following technical advantages:

1. that the present invention uses stationary acquisition mode in place of traditional mechanical rotatory acquisition mode, by means of controlling the scanning x-ray sources to sequentially change directions which is equivalent to data acquisition of speedy rotatory scan, to significantly improve scan speed;

2. that the present invention significantly reduces the manufacturing difficulty by avoiding centrifugal force caused by mechanical rotation, and thus decrease signals motion trail, overlap and crosstalk in high speed rotation;

3. that the present invention could fulfil data acquisition in divided areas, thereby enhancing the accuracy and speed of imaging, which enable the patients to be diagnosed with safer dose that is less than an effective dose;

4. that the present invention could collect energy spectrum signals (energy distribution data), measuring the energy spectrum of single photon; and could achieve material information of the tested object to speculate atomic number of the material;

5. that the present invention greatly reduces the scattering interference to the signal by the narrow beam x-ray directing onto a smaller area of a photon-counting detector, and provides a low dose high performance imaging solutions with high signal to noise ratio in lower doses.

BRIEF DESCRIPTION OF THE DRAWINGS

FIGS. 21A, 21B, 21C and 21D show various scan timing and scan speed in the present invention;

DETAILED DESCRIPTION OF THE PREFERRED EMBODIMENTS

The present invention is described in further detail below with reference to accompanying drawings and specific embodiments.

Figure 1:
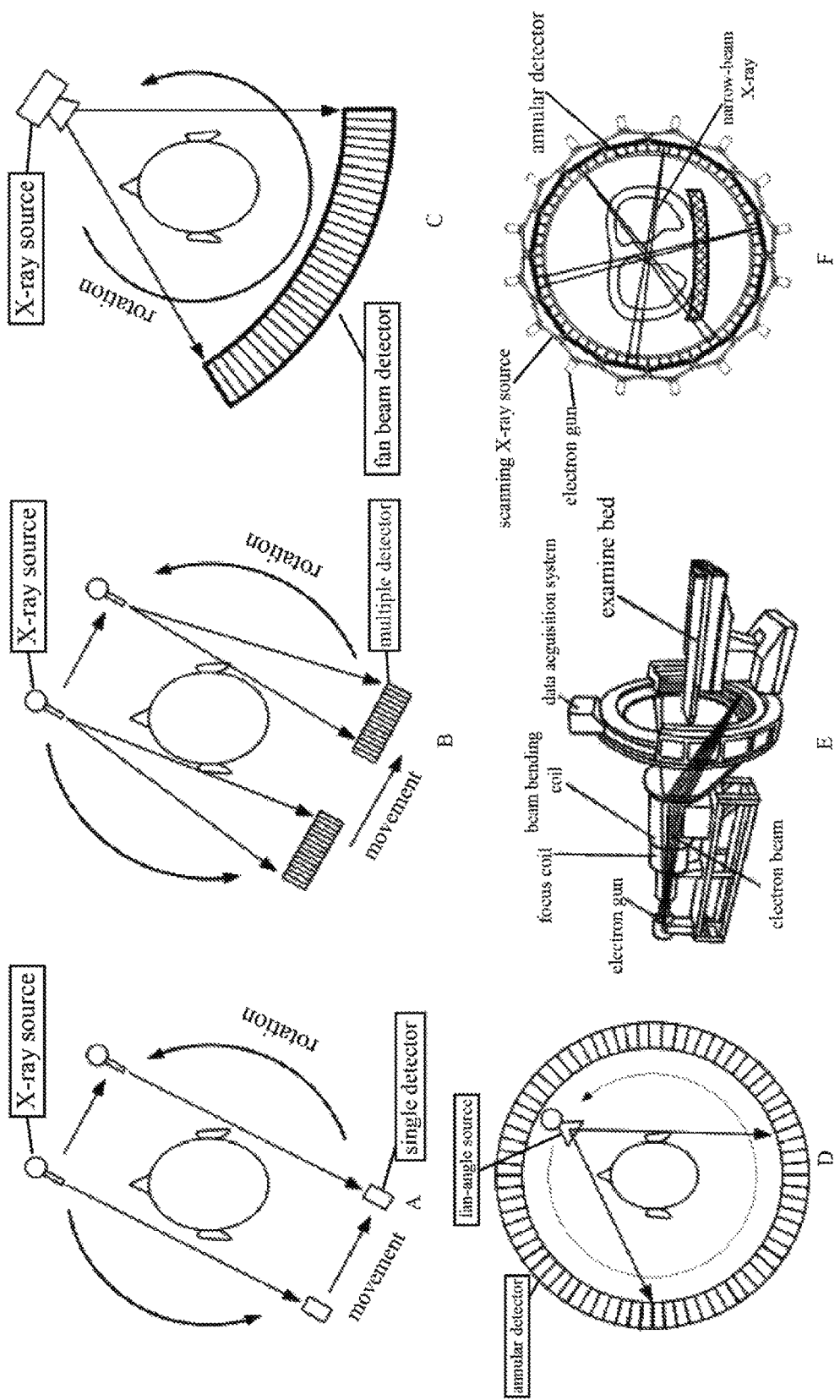
FIG. 1 is a structure comparison illustration between first five generations of the CT imaging systems and the present stationary real-time CT imaging system.
Figure 2:
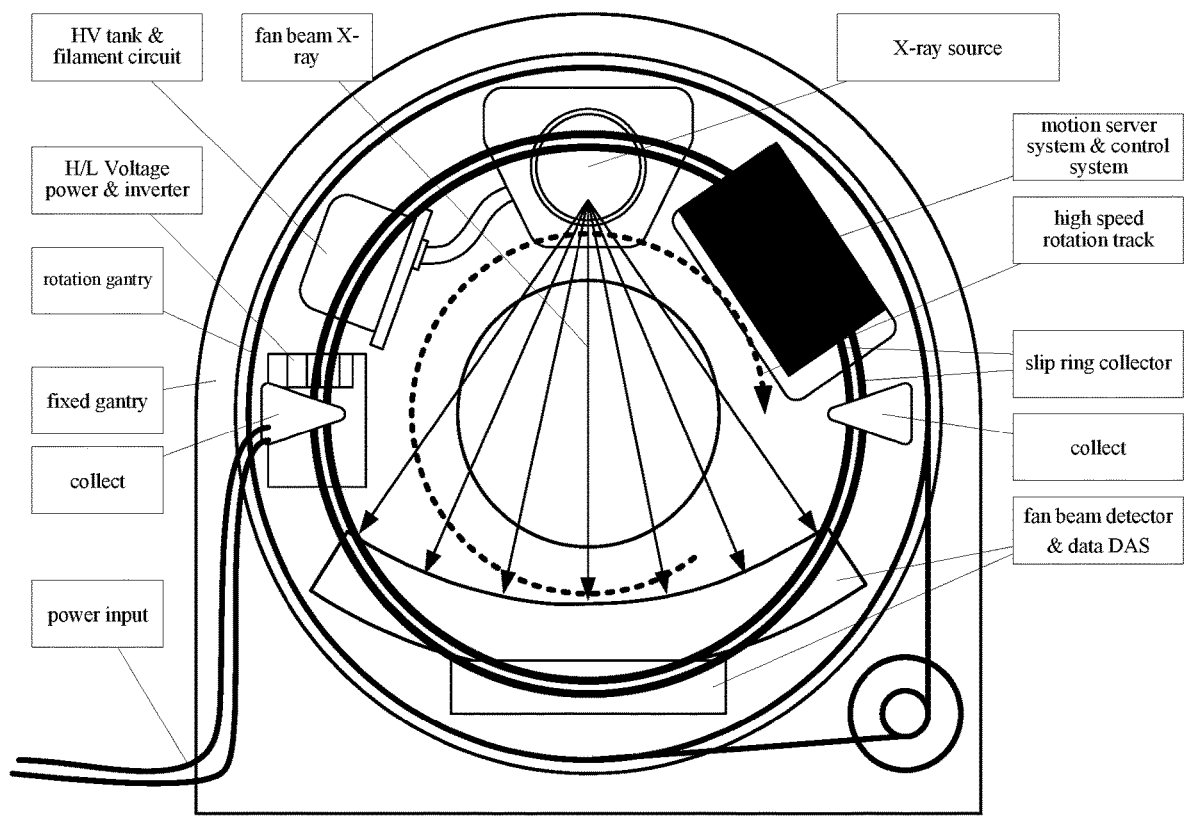
FIG. 2 is a structure schematic diagram of a typical fan-beam CT imaging system.
Figure 3A:
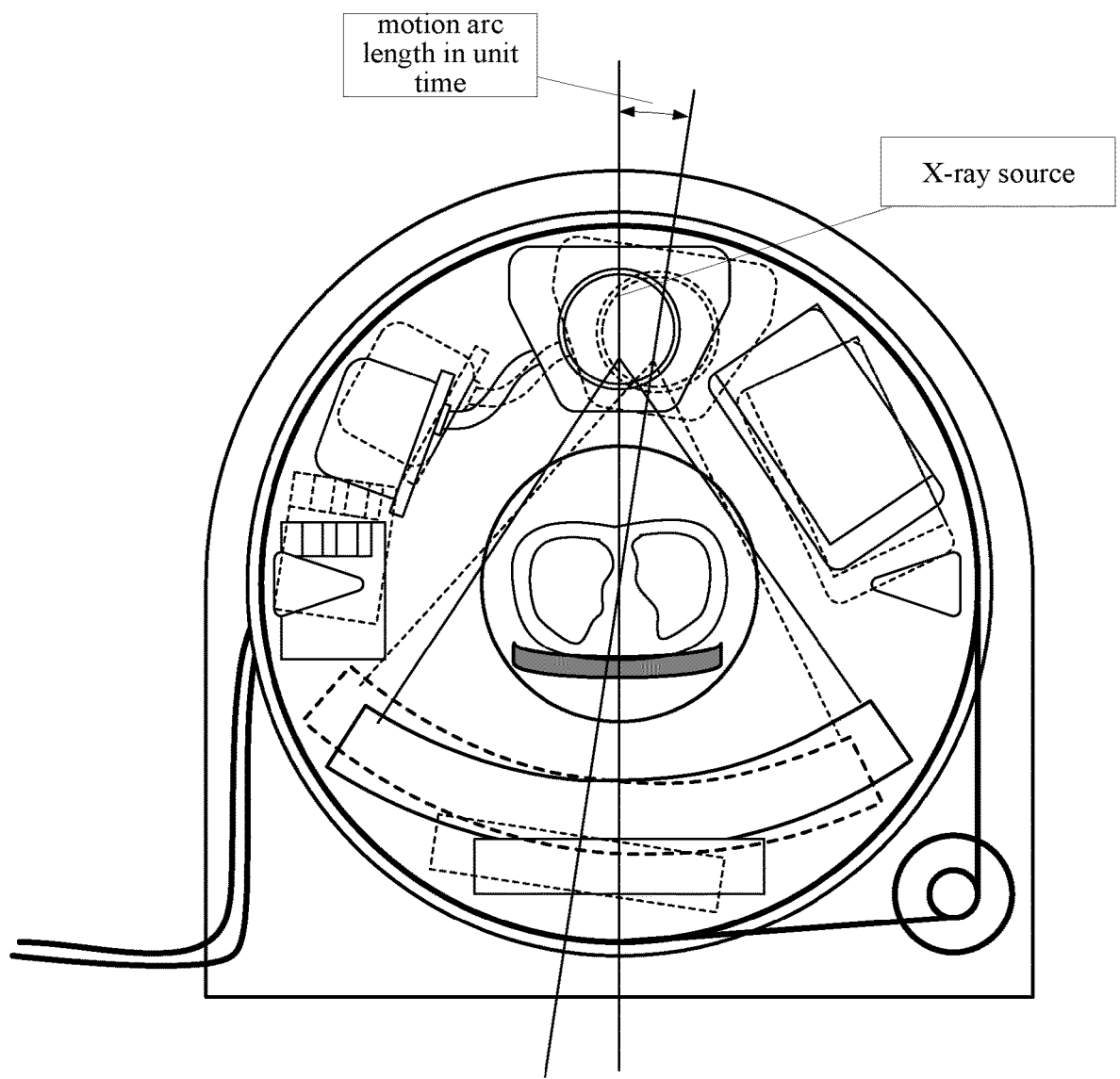
FIG. 3A and FIG. 3B are schematic diagrams of motion trail caused by speedy rotation of the traditional CT imaging system.
Figure 3B:
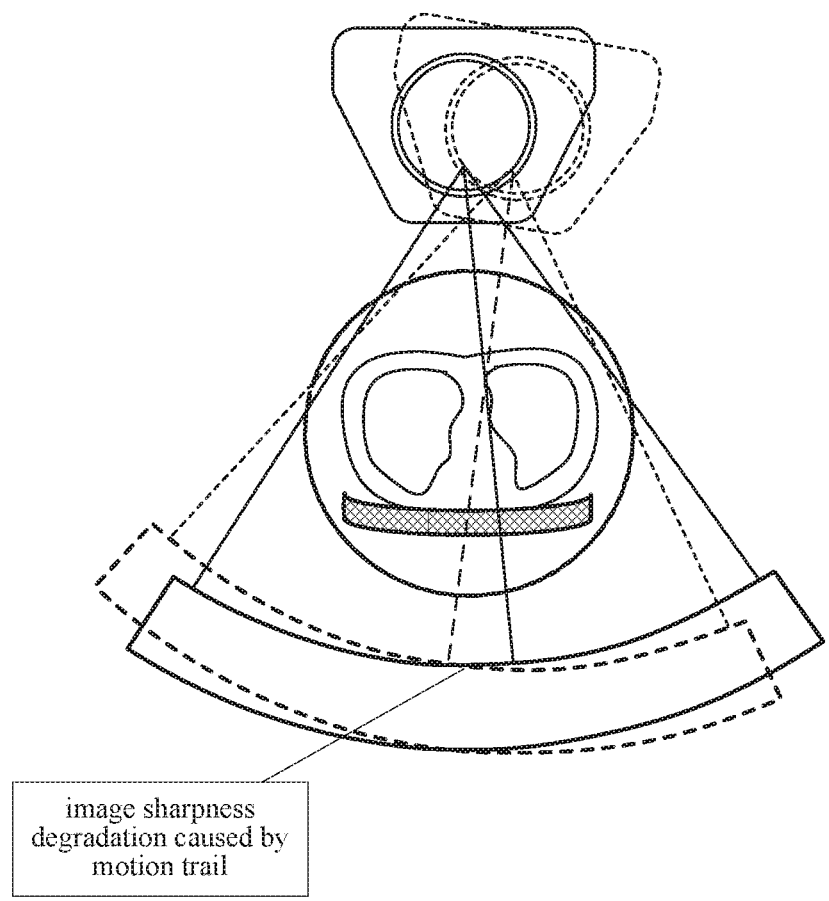
Figure 4:
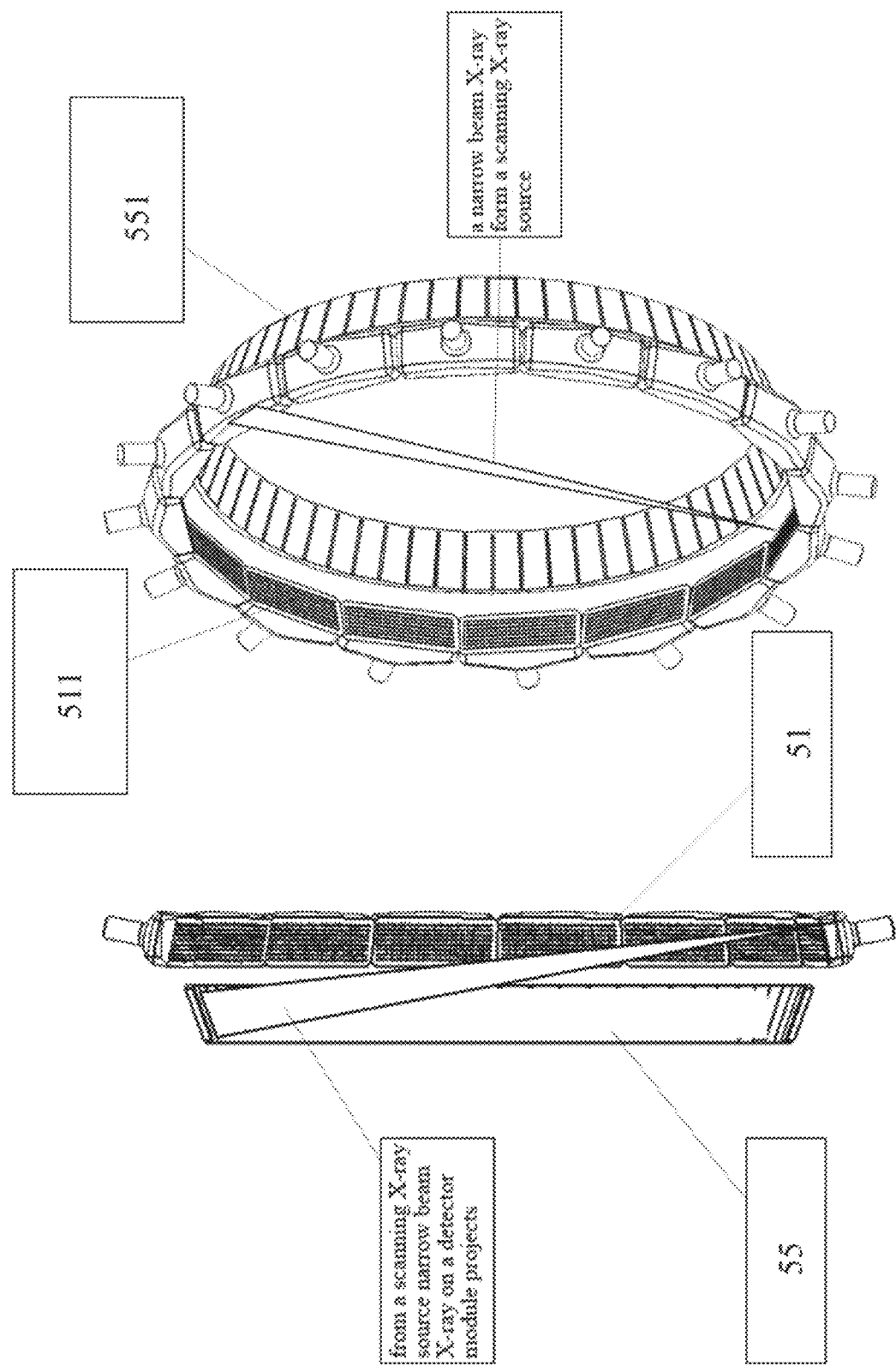
FIG. 4 is a structure schematic diagram of an annular scanning x-ray source and an annular photon-counting detector of the present invention.

As shown in FIG. 4, the present invention provides stationary real-time CT imaging system 100 which includes a parallel set of annular scanning x-ray sources 51 (referred to annular x-ray source) and annular photon-counting detectors 55 (referred to annular detector). The annular scanning x-ray source 51 and the annular photon-counting detectors 55 (further explained below) do not locate in the same plane, but in different planes parallel to each other. Their ring structures are concentric. In other words, the normals respectively penetrating the centers of their ring structures coincide with each other. This design can prevent the x-ray beams from the scanning x-ray source to the photon-counting detector from being interrupted by an overlapped structure, and can ensure pencil-beams (also known as narrow beams hereafter) x-ray from each x-ray source direct onto a photon-counting detector module. To ensure that the scanning x-ray sources in parallel can accurately point to the corresponding photon-counting detectors, the scanning x-ray sources and/or photon-counting detector have a certain ramp angle. The ramp angle could be selected by those skilled in this technology field in conventional way, and is not described in detail.

Figure 5:
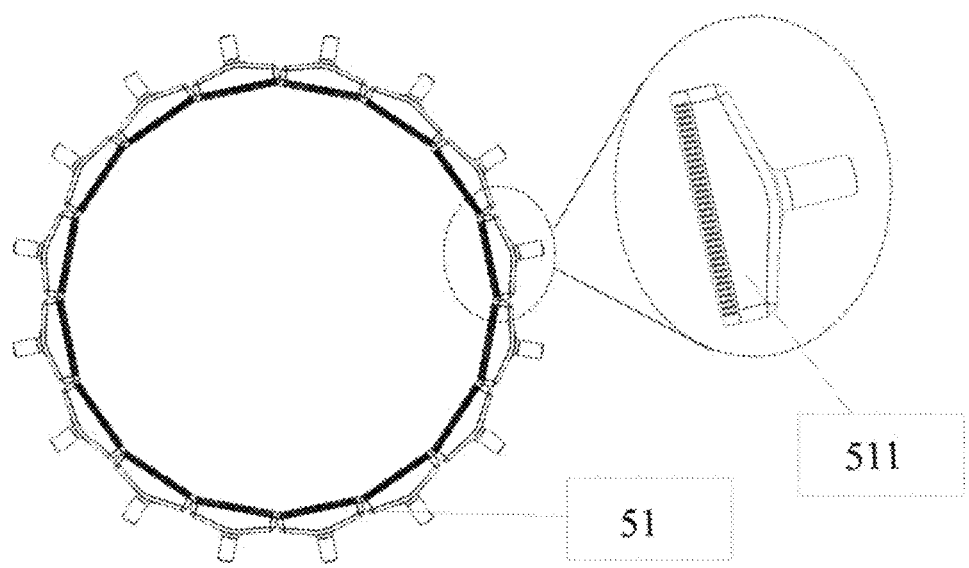
FIG. 5 is a structure schematic diagram of an annular scanning x-ray source of the present invention.

FIG. 5 illustrates a structure of an annular scanning x-ray source 51. The annular scanning x-ray source 51 comprises a plurality of scanning x-ray sources 511, which closely arrayed in a ring to form a ring structure. In present invention, the annular scanning x-ray sources 51 are multiple focus x-ray source instead of traditional single focus x-ray source, and emit narrow beam of x-rays instead of traditional broad-beam x-rays in the case without the need for a large field of vision. Between the x-ray source and the detector is the reverse geometric imaging mode. Individual scanning x-ray source 511 has enough x-ray emission focus. Alignment holes 5110 of each scanning x-ray source 511 direct respectively to the annular photon-counting detector that is formed by a plurality of photon-counting detector modules 551. Each scanning x-ray source emits narrow beam x-ray to a corresponding photon-counting detector module, and can emit according to a variety of timing.

Figure 6:
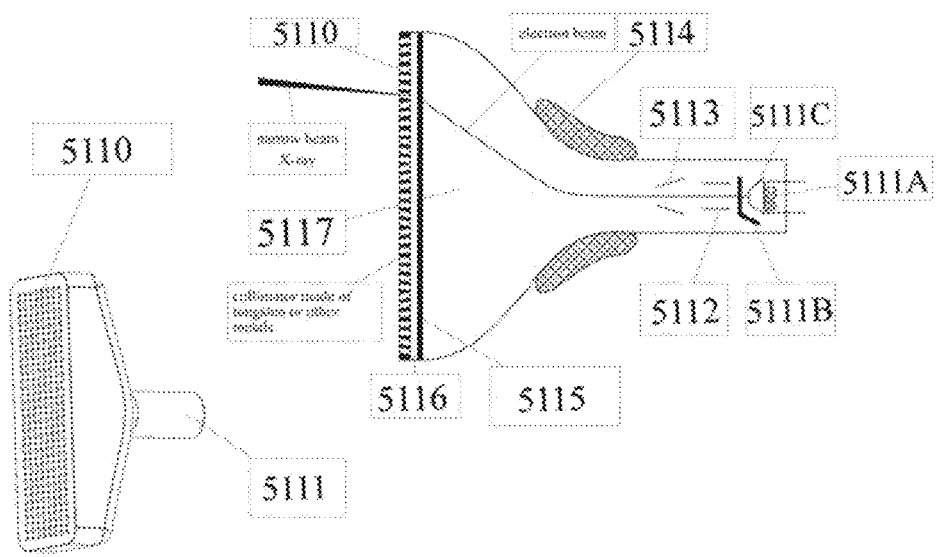
FIG. 6 is an inside structure schematic diagram of single scanning x-ray source of the present invention.

FIG. 6 shows a basic structure of a single scanning x-ray source 511, including electron gun 5111, focusing anode 5112, accelerating anode 5113, deflection coil 5114, high voltage anode 5115, a beryllium window 5116, vacuum chamber 5117 and the alignment holes 5110s. Each electron gun 5111 includes filament 5111A, grid-controlled cathode 5111B, focus cathode 5111C and other elements. The filament 5111A, grid-controlled cathode 5111B, focusing anode 5112, accelerating anode 5113, the high voltage anode 5115 (for example the tungsten target) and other elements are installed in the vacuum chamber 5117, to ensure that the flight path of the electron beam is completed in the vacuum chamber 5117. The scanning x-ray source 511 works in this way: the filament 5111A heats the focus cathode 5111C; free electrons emit from the focus cathodes 5111C heated; the electrons are allow to pass when voltage of grid-controlled cathode 5111B is higher than that of the focus cathode 5111C, and are prevented to pass when the voltage of the grid-controlled cathode 5111B is lower than that of the focus cathode 5111C. When grid-controlled cathode 5111B's positive bias is on, electrons pass through a focusing anode 5112, and the focusing anode 5112 focus the electrons. The accelerating anode 5113 accelerates the electrons focused, the deflection coil 5114 adjusts direction of the accelerated electron beam. The deflection coil 5114 includes a row deflection coil and a column deflection coil to adjust the electron beam in X direction and Y direction. Finally, the electron beam strikes on a target of the high voltage anode 5115. The high voltage anode 5115 is made of tungsten or other higher atomic number materials. When the electron beam strikes on the high voltage anode materials, the electrons decelerate abruptly to produce x-rays. The x-rays go through the beryllium window 5116 into the alignment holes 5110 to be constraint and adjusted, form very thin narrow-beam x-rays directing to the photon-counting detectors. Each electron gun 5111 has alignment holes 5110 in M columns, N rows, where M and N are positive integers.

Figure 7:
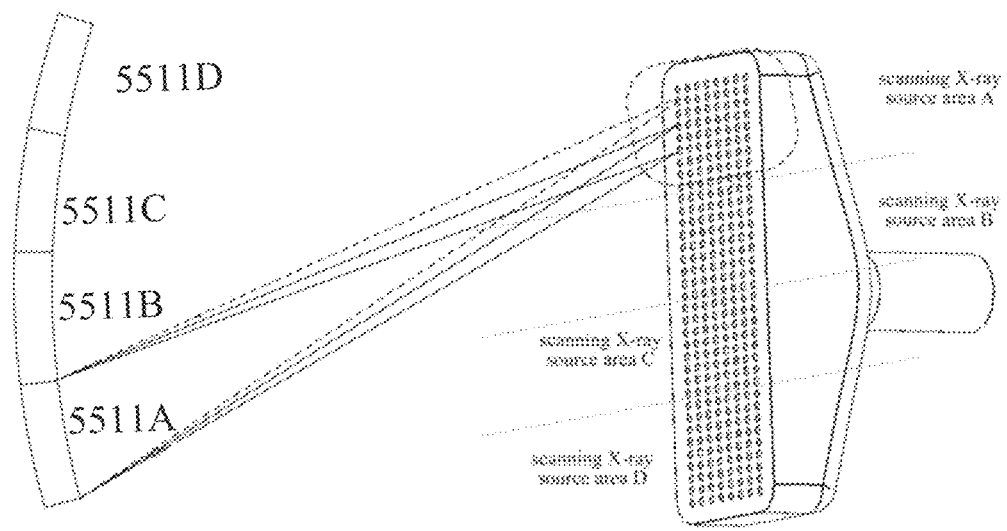
FIG. 7 is a schematic diagram of area arrays and scan sequences of the single scanning x-ray source of the present invention.

FIG. 7 shows single scanning x-ray sources area in arrays and scan sequence diagram. In the present embodiment, each scanning x-ray source 511 corresponds to a plurality of photon-counting detector modules. Each scanning x-ray source 511 is divided into multiple areas, each photon-counting detector module 551 includes a plurality of photon-counting detector. Within each scanning x-ray sources area, all focus alignment direction of the x-rays direct to an identical photon-counting detector unit 5511. In FIG. 7, scanning x-ray source area A directs to photon-counting detector unit A, scanning x-ray source area B directs to photon-counting detector unit B, and so on. The scanning x-ray sources 511 can emit point-by-point or at every other point (dot interlacing), or emit line by line or at every other line (alternate line), according to commands from a scan timing controller 41. Multi-focus x-ray beams from one area of the scanning x-ray source 511 direct by turns onto a corresponding photon-counting detector unit 5511, so as to correspondingly get multiple sets direction data on the photon-counting detector unit 5511. Thus, three-dimensional reconstruction within the narrow beam scanning x-ray source area could be achieved by processing of these direction data. Therefore, when multiple areas in each of the multiple scanning x-ray sources direct in parallel onto the corresponding photon-counting detectors units 5511, the photon-counting detector units 5511 can parallelly get multiple sets of direction data to complete much more narrow-beam three-dimensional reconstruction. All photon counting detector modules 551 distributed along a circle can complete collection and reconstruction of the x-ray beams within a short time (called frame cycle). The x-ray beams are emitted from focus of the corresponding scanning x-ray source 511. Consequently, within a frame cycle, all of the photon counting detector units 5511 parallelly completed narrow beam reconstruction of the corresponding scanning x-ray source areas. The narrow beam reconstruction is accumulated to be reconstruction of a full scanning x-ray source area. Theoretically, on condition that all scanning detectors work in parallel and each photon detector unit 5511 fulfills a parallel gathering, a frame cycle times can be shorted to a period of a scanning x-ray source area focus emission. That is, a frame cycle can be within 10 or more milliseconds.

Figure 8:
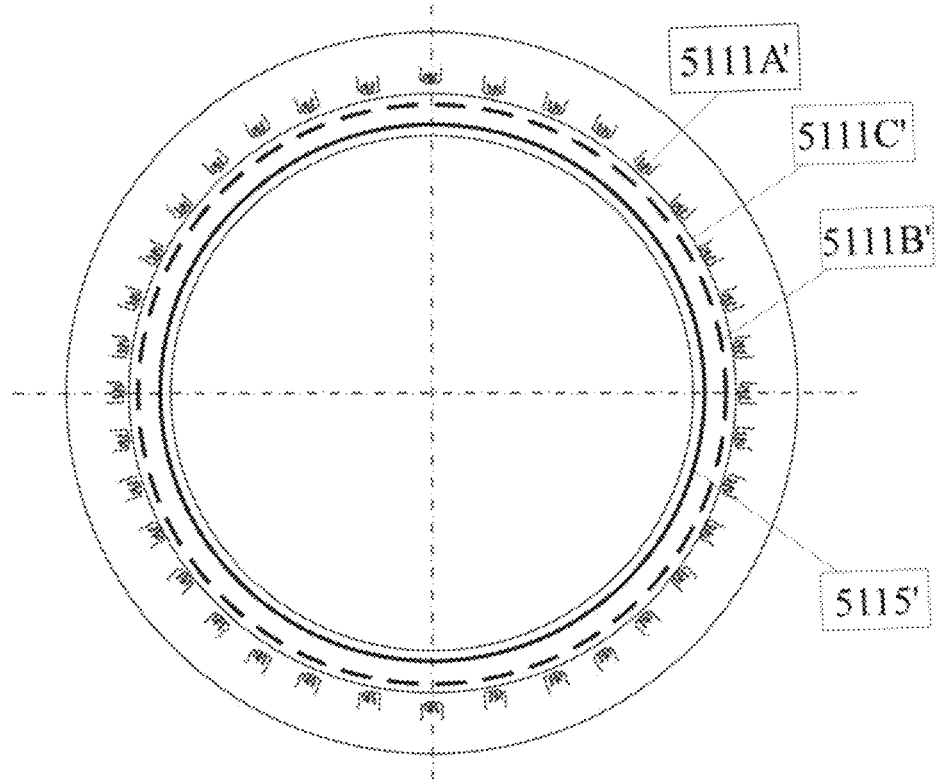
FIG. 8 is a structure schematic diagram of an annular x-ray source of the present invention.

The scanning x-ray sources 511 in the present invention can be replaced by a multi-focus ring x-ray sources. As shown in FIG. 8, the ring x-ray sources includes a plurality of filaments 5111A' arrayed in a ring, wherein a plurality of cathodes 5111C' connected to each other to form a ring (the ring-shaped cathode) and the filaments 5111A' locate outside the ring-shaped cathode. A plurality of control grids 5111B' inside the ring-shaped cathode 5111C' correspond to the filaments 5111A' one by one, and are arranged in turns to form a ring that is concentric to the ring formed by the cathodes. Inside the ring of the control grids 5111B', there is a ring-shaped anode target surface 5115' that is also concentric to the ring formed by the cathodes. When the control grid bias voltage is negative, electrons of the cathode will not flow to the anode target surface; when the control grid bias voltage is positive, electrons of the cathode flow in high speed to the anode target surface in an electric field. The electrons strike the anode target surface 5115' to produce narrow-beam x-ray directing to the photon-counting detector units 5511 on the target surface.

Figure 9:
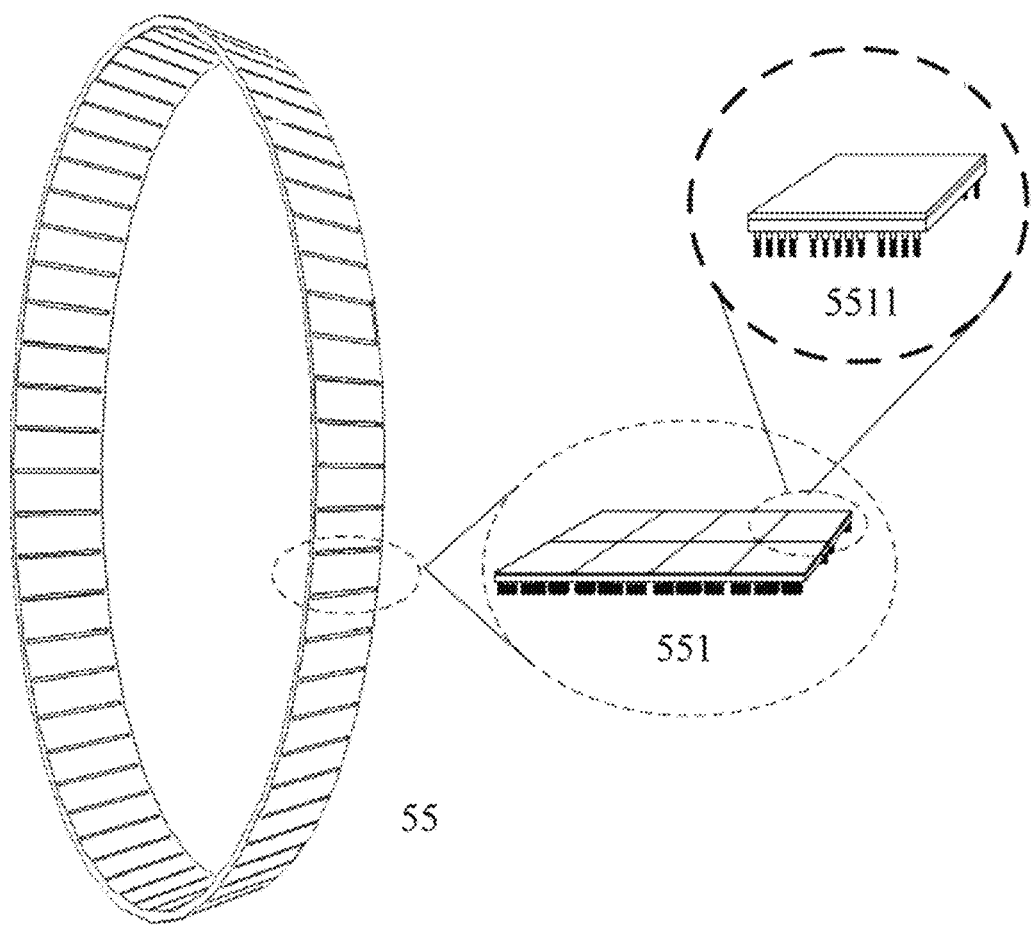
FIG. 9 is a structure schematic diagram of the annular photon counting detector of the present invention.

In order to accurately collect exposure information from the annular scanning x-ray source 51 mentioned above, the present invention provides an annular photon counting detector 55. FIG. 9 shows the basic structure of the annular photon counting detector 55. The annular photon counting detector 55 includes a plurality of photon counting detector modules 551, which are connected to each other to form a ring. Each photon counting detector module 551 includes a plurality of photon counting detector units 5511. The photon counting detector module can work in synchronization with the corresponding scanning x-ray source 51, or work alternatively with the corresponding scanning x-ray source 51 according to commands from the scan timing controller 41. In the present invention, the photon counting detector units 5511 have high detection sensitivity on single-photon x-ray pulse signals, so that they can execute event-detection, counting, energy-identify to the single-photon x-ray pulses while reducing the effects of noise on signal collection. Each photon-counting detector module 551 has independent data acquisition module 5512 and data transmission channel 5513. Therefore, data can be initially processed and rearranged within the photon-counting detector module 551, to reconstruct narrow-beam x-ray data. Each photon-counting detector unit 5511 executes single-photon detection to the x-ray beam under the comprehensive management of the data acquisition module 5512 and the data transmission channel 5513, and collects the data to a photon-counting detector module 551. All data rearranged or reconstructed by the data acquisition modules 5512 are transmitted to the preprocessor through the data transmission channel 5513.

The data from all data acquisition module 5512 and the data rearranged or reconstructed by the data acquisition module 5512 could be reconstruction to a data frame in the data preprocessor in real-time, and are then sent to the main processor 4. In the data transmission, the data preprocessed by the data preprocessor 56 are transmitted through the data transmission channel 5513 to the main processor 4, usually in GHz or THz frequency for high-speed data transfer, so parallel multi-channel optical fiber transmission channels or Giga e network cable are needed.

In the present invention, annular photon counting detectors 55 divide 0~360° of the circumference into multiple areas and collects the data of those areas in synchronization under the timing control, which greatly improve the data collection speed for all signals on a circle and thus make it possible to reconstruct image. Therefore, the present invention overcomes the disadvantages of conventional CT imaging systems that the mechanical rotation characteristics of conventional CT imaging systems have to collect data in a sequence from 0° direction angle to 360° direction angle in accordance to a rotation sequence. In the present invention, no matter what degree the data speed is, data acquisition range corresponding to each photon-counting detector units is unchanged and corresponds with the physical dimensions thereof. In addition, the stationary real-time CT imaging system of the present invention may not collect the data in a sequence from 00 to 360°. It may be carried out in varied way according to the actual needs to better meet the clinical requirements. The data collecting density especially for important parts' direction differs from that for less important parts' direction, so as to save x-ray dose and ensure data integrity for important details.

Figure 10:
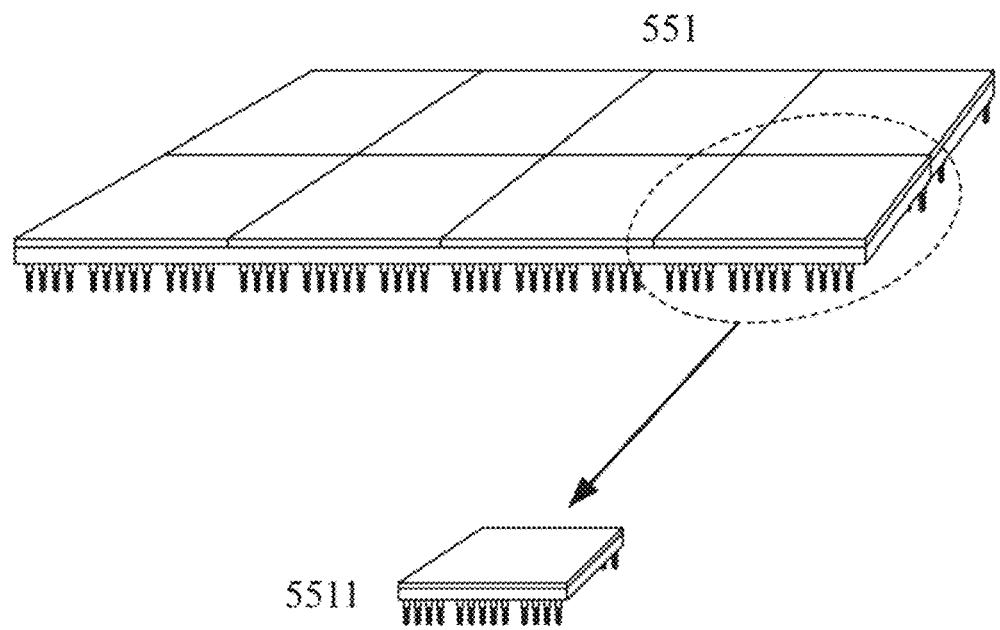
FIG. 10 is a structure schematic diagram of the photon-counting detector module of the present invention.
Figure 11:
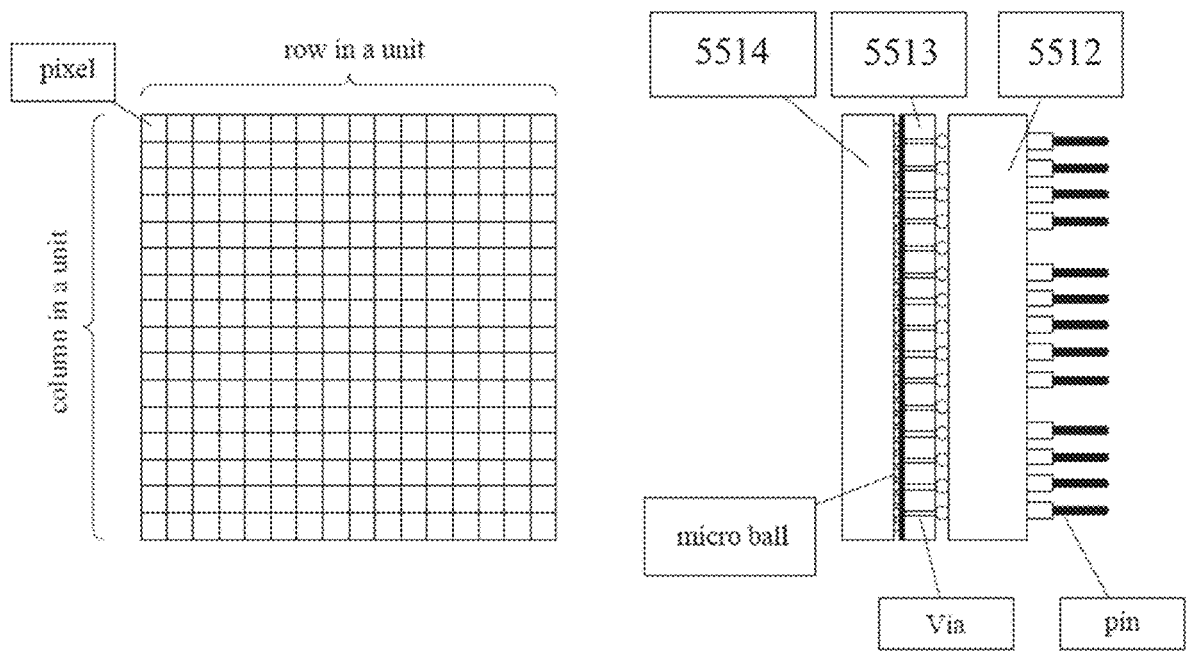
FIG. 11 is a structure schematic diagram of the photon-counting detector unit of the present invention.

FIG. 10 illustrates a structure of a single-photon counting detector module 551. Each photon-counting detector module 551 includes a plurality of photon-counting detector units 5511. Each photon-counting detector unit 5511 includes x-photon sensitive material (cadmium zinc telluride, single crystal silicon, gallium arsenide, amorphous selenium, etc.) element and an analog-digital mixed integrated circuit connecting with the x-photon sensitive material element. The analog-digital mixed integrated circuit is made of CMOS devices. FIG. 11 shows the basic structure of the photon-counting detector unit 5511, which includes a PCB board 5512, photon-counting ICs 5513 and an x-photon detection layer 5514. The PCB board 5512 connects with pins to facilitate replacement or maintenance. There are silicon substrate vias 5515 between photon-counting ICs 5514. The x-photon detection layer 5514 has a plurality of pixel electrodes (not shown) binding with the photon-counting IC 5513 with micro balls 5516. The x-photon detection layer 5514 is made from cadmium zinc telluride, single crystal silicon, gallium arsenide, amorphous selenium or other photon sensitive materials. The data acquisition range for each photon-counting detector unit 5511 is unchanged, and corresponds to the physical size. Therefore, the present invention avoid motion trail because each photon-counting detector unit 5511 accurately collects data in a fixed area. In the traditional CT imaging system, the motion trail often occurs due to too large displacement in per unit time as the rotation speed increase.

Each photon-counting detector unit 5511 is made up of M rows and N columns, so it has M*N pixels (corresponding to the distribution of the alignment holes), wherein M and N are positive integers. Each pixel fulfills event detection, signal amplification, identification of energy, and photon-counting functions. Therefore, the photon-counting detector can distinguish energy as well as space in high accuracy. The size of each pixel can be designed in 1~1000 um. The smaller the pixel is, the higher spatial resolution is. Meanwhile, data size becomes greater and greater on unit area (in cost of speed decrease in data acquisition and reconstruction). In one embodiment of the present invention, the photon-counting detector unit 5511 preferably uses 330 um*330 um pixels to meet the accurate scan requirements of full-body-scan and body-organ-scan (such as the coronary arteries). By way of using photon-counting detector unit, absorption signal strength data and energy distribution data can be simultaneously acquired. The absorption signal strength data can be used to reconstruct three-dimensional images and various visual effects according to CT Number, gray-scale dimensions. The energy distribution data can be used to calculate atomic number of the substance on each voxel location, to form energy resolving power of energy spectrum dimension and image palette.

Figure 12:
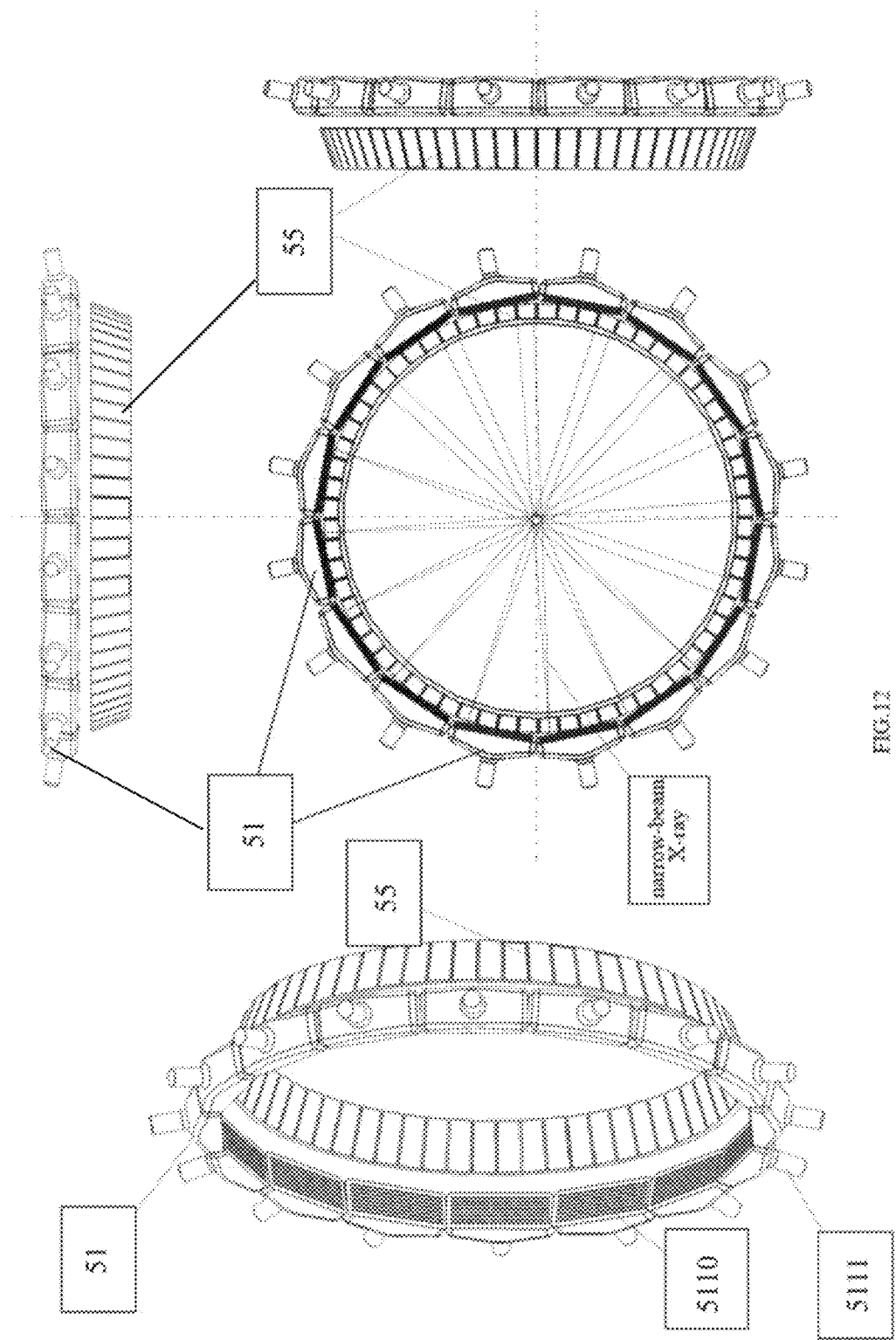
FIG. 12 is a structure of a scan host of the annular scanning x-ray source of the present stationary real-time CT imaging system.

Based on the above-mentioned annular scanning x-ray source 51 and annular photon-counting detector 55, the present invention further provides a stationary real-time CT imaging system 100. FIG. 12 shows the structure of scan host of the stationary real time CT imaging system 100. The stationary real time CT imaging system mainly comprises an annular scanning x-ray source 51 and an annular photon-counting detector 55. The annular scanning x-ray source 51 includes a plurality of scanning x-ray sources 511 and the annular photon-counting detector 55 includes a plurality of photon-counting detector modules 551. Because the stationary real-time CT imaging system 100 realizes x-ray beam rotating scanning in high speed without rotating parts, all x-ray emission focuses and the photon-counting detectors are fixed during the scanning process, radically eliminates motion artifacts and motion tail. In addition, the narrow beam x-rays are emitted in turns so that the influence of scattering is further reduced and high-energy-resolving-power data collection and high-speed real-time reconstruction can be achieved.

Figure 13:
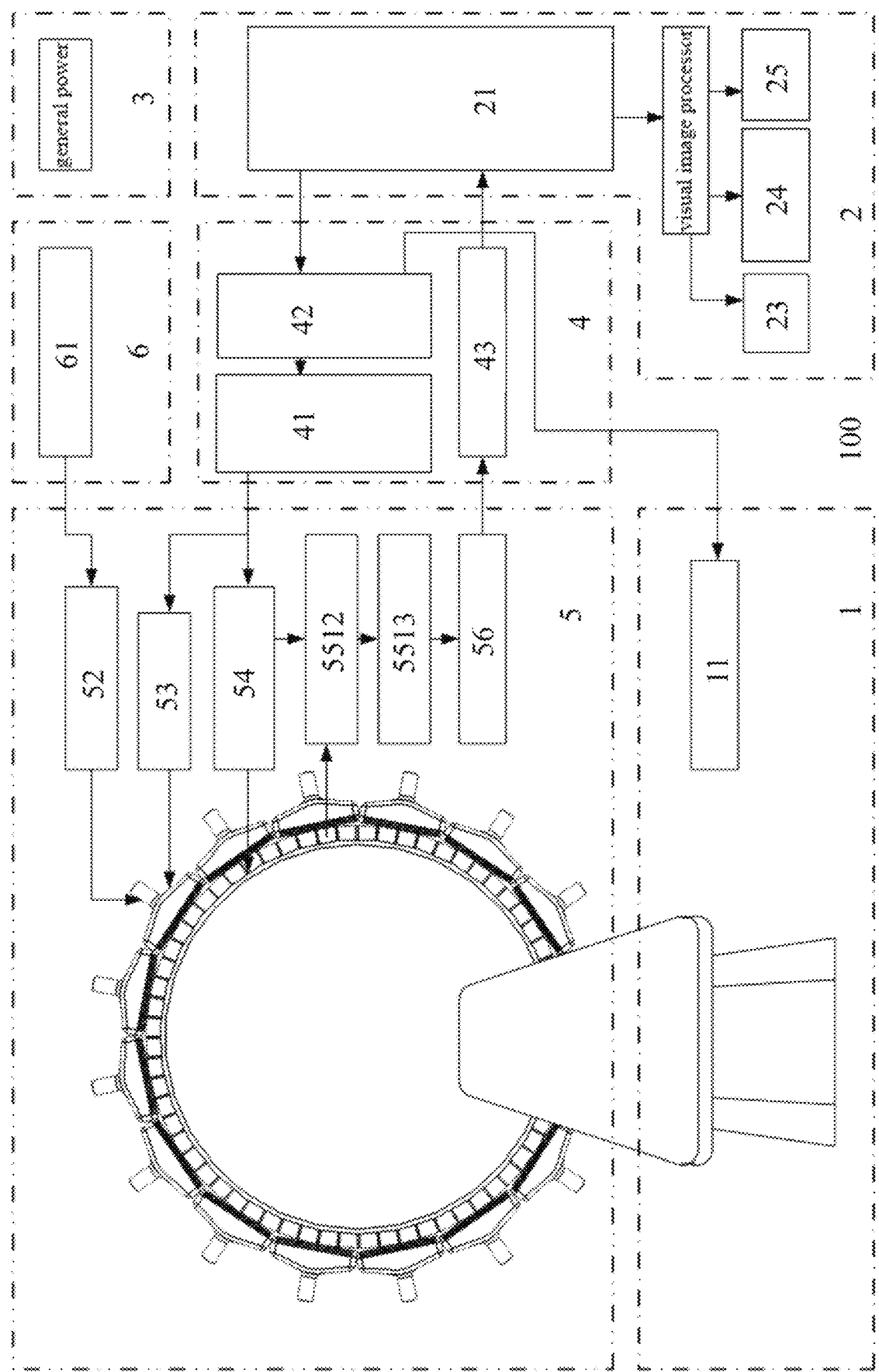
FIG. 13 is a schematic diagram of the present stationary real-time CT imaging system.

FIG. 13 illustrates the schematic structure of the stationary real time CT imaging system 100, which includes a bed control unit 1, a CT hosts and interface unit 2, a power control unit 3, a high voltage control unit 6, a main processor 4 and a scan host 5. The scan host 5 has parallel annular scanning x-ray sources 51 and annular photon counting detectors 55, as well as a high speed grid controller 52, a line field deflection controller 53 (field deflection controller for a line), a photon-counting detector controller 54, a multi channel photon-counting detector acquisition circuit 5512, and multi-channel data transmission channels 5513 and a data preprocessing module 56. The main processor 4 includes a scan timing controller 41, a multi-mode scan timing generator 42 and a high speed data transmission channel 43. The CT hosts and interface unit 2 includes a real time reconstruction system and main control computer 21, a visual image processor 22, a control display 23, a reconstruction display 24 and a multi-mode display 25. The bed control unit 1 includes a bed motion control module 11. The high voltage control unit 6 includes a high voltage direct current generator 61 (HV DC generator).

The HV DC generator 61 connects with a tungsten anode target. The HV DC generator 61 generates HV DC signals to the anode tungsten target 5115 of the scanning x-ray sources 511. Therefore, high potential difference is generated between the focus cathode 5111C and anode tungsten target 5115 in the electron gun 5111. The high speed grid controller 52 is connected to a grid-controlled cathode 5111B of each scanning x-ray source 511. The electron beams emitted by the electron gun 5111 are controlled by the grid-controlled cathode voltage, and travel under control of the row filed deflection controller and the deflection coil to strike the anode tungsten target 5115 and thus produce narrow beam x-rays. The real time reconstruction system and main control computer 21 connects with the multi-mode scan timing generator 42, the scan timing generator 42 connects with the scan timing controller 41, which connects with the line field deflection controller 53 and the photon-counting detector controller 54. The scan timing controller 41 in the present invention is similar to that in conventional CRT display. Their difference is that grid control is newly applied in the present invention to achieve sequential scanning and reduce heat, form high voltage pulse for a short time (generally between 0.1~20 microseconds), and generate high quality narrow beam x-ray. The line field deflection controller 53 connects with the deflection coil 5114 of the scanning x-ray source 511; the photon-counting detector controller 54 connects with every photon-counting detector module 551. The photon-counting detector controller 54 connects with multi-channel photon-counting detector acquisition circuit 5512. The photon-counting detector module 551 completes initial processing after the data acquisition, and then sends the data to the multi-channel photon-counting detector acquisition circuit 5512. The multiple data transmission channels 5513 are input the data from the photon-counting detector acquisition circuit 5512, and send the data to the data preprocessor 56. The data preprocessor processes the data from the multiple data transmission channel 5513 to fulfill data frames' integration and reordering, and then transmits to the high speed (HS) data transmission channel 43 in frame queues. The data is channeled to the real-time reconstruction and main control computer 21 via the high-speed data transmission channel 43. The bed motion control module 11 connects with the scan timing generator 42 of the main processor 4. The real time reconstruction system and main control computer 21 reconstructs an image using the data, and then transmits the image to the control display 23, reconstruction display 24 and multi modal display 25 for display via the visual image processor 22.

Figure 14:
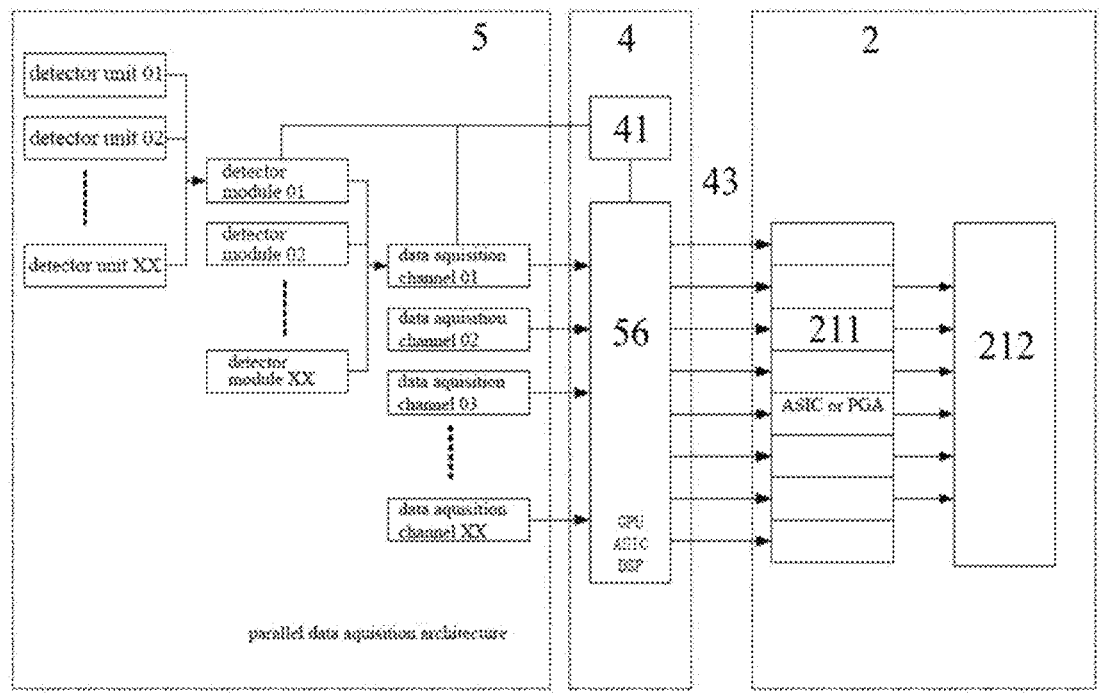
FIG. 14 is a diagram of data parallel processing of the present stationary real-time CT imaging system.

FIG. 14 shows a parallel data processing flow chart of the scan host 5, the main processor 4, and the CT host and interface unit 2. The scan host 5 includes a plurality of photon-counting detector modules 551, multiple scanning x-ray sources 511, a high speed grid controller 52, a line field deflection controller 53, a photon detector controller 54, multiple detector acquisition circuits 5512, multiple data acquisition channels 5513 and a data preprocessor 56. Each photon-counting detector module 551 has a plurality of photon-counting detector units 5511. As mentioned above, main processor 4 includes the scan timing controller 41 and the high-speed data transmission channel 43. The CT host and interface unit 2 includes the real-time reconstruction and main control computer 21, and visual image processor 22. The main control computer 21 includes a parallel reconstruction module 211 fulfilling data parallel reconstruction, and a storage device 212 storing the voxel data. The scan host 5 includes a plurality of photon-counting detector modules 01~XX (XX is a positive integer, the same below). Each photon-counting detector module 551 contains a plurality of photon-counting detector units 5511, for example, the photon-counting detector module 01 including photon-counting detector units 01~XX. In a preferred embodiment of the present invention, each photon-counting detector module 551 has 4*8=32 photon-counting detector units 5511, and each photon-counting detector unit 5511 has 32*32-photon-counting detector pixels. The size of each pixel is 400 um*400 um. Dimension of each photon-counting detector module is 51.2 mm*102.4 mm. The annular photon-counting detector 56 has 50 photon counting detector modules 551, and its diameter is about 800 mm, its width is about 102.4 mm. Each of the multiple data transmission channels 5513 corresponds to one or more photon-counting detector modules 551. The data acquired by the photon-counting detector modules 01~XX are transferred via data transmission channels 01~XX to the data preprocessor 56 in the scan host 5. The data preprocessor 56 includes GPU, ASIC and DSP. The data preprocessor 56 conducts frame data preprocessing on the original pixel exposure information from the data trasmission channels or the data after data rearrangement and data correction, to form a frame data. The frame data are then transmitted to the parallel reconstruction module through the parallel high speed data transmission channels 5513. The parallel reconstruction module 211 has multiple parallel GPUs or ASICs. It reconstructs the frame or block data into voxel data. Since the process is multi-channel parallel processing, reconstruction speed can meet real-time visualization requirements.

Figure 15:
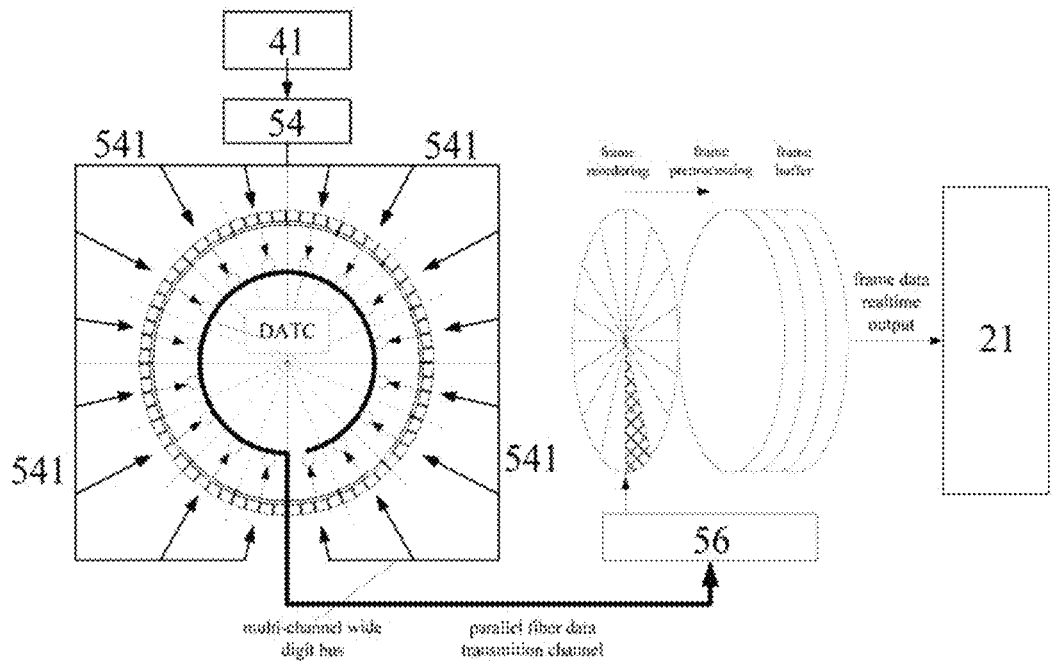
FIG. 15 is a diagram of data processing and data reconstruction of the present invention.

As shown in FIG. 15, the detector controller 54 controlled by the scan timing controller 41, via acquisition command channels 541, sends an acquisition command to the photon-counting detector module 551 to acquire pixel exposure information. The independent acquisition command channels 541 are multi-channel wide digit buses, so as to assure all of the data acquisition modules receive the acquisition commands parallelly and in synchronization. The frame data acquired are data within a frame period. Pixel information integration to the acquired pixel exposure information data is executed by the photon-counting detector unit 5511, and then secondary integration and processing are executed by the photon-counting detector module 551. The secondary integration and processing include data mosaic and pixel data correction by the photon-counting detector module. Finally, narrow-beam x-ray data after the integrations or initial reconstruction are transmitted to the data preprocessor 56, through parallel fiber data transmission channels by the photon-counting detector modules 551. The data preprocessor 56 executes data processing to the narrow-beam x-ray data from different photon-counting detector modules 551, including frame reordering, frame correction, frame buffer and frame output in real time. The real-time output frame data are transmitted to the real-time reconstruction system and main control computer 21. The data preprocessor 56 processes the data from multiple photon-counting detector modules 551 into complete frames and blocks, and then send to the main control computer in the data frame and the data block format. The data frame refers to a data layer covering the full range of 360°, and the data block refers to an array of these data layers. Such a data preprocessing mechanism is intended to complete initial processing to some data before they are transferred to the main control computer, compile the data acquired in different acquisition sequences into frame and data block format, and send them to the main control computer in standard frame or block data structures. Sometimes, the data pre-processing to the frame or data block could be partially executed in the data preprocessor 56, or in the main control computer 21 after they are transmitted to there. The preprocessing of this part data includes, but is not limited to a single pixel offset correction, hardening correction, flat field correction, frame or block data geometric correction, time drift correction, energy correction, scattering suppression.

In the conventional Multi-slice spiral CT, the x-ray sources needs to be continuously rotated so that it is by means of slip ring contact or wireless communication that the data are transmitted to the computer during the rotation process. Compared with the existing multi-slice spiral CT, the stationary real-time CT imaging system 100 in the present invention uses speedy and reliable optical fiber to realize parallel data transmission, which increases data flow, data reliability, system simplification, reliability and consistency of the product. This can effectively guarantee the three dimensional reconstruction algorithm's real time ability.

Figure 16:
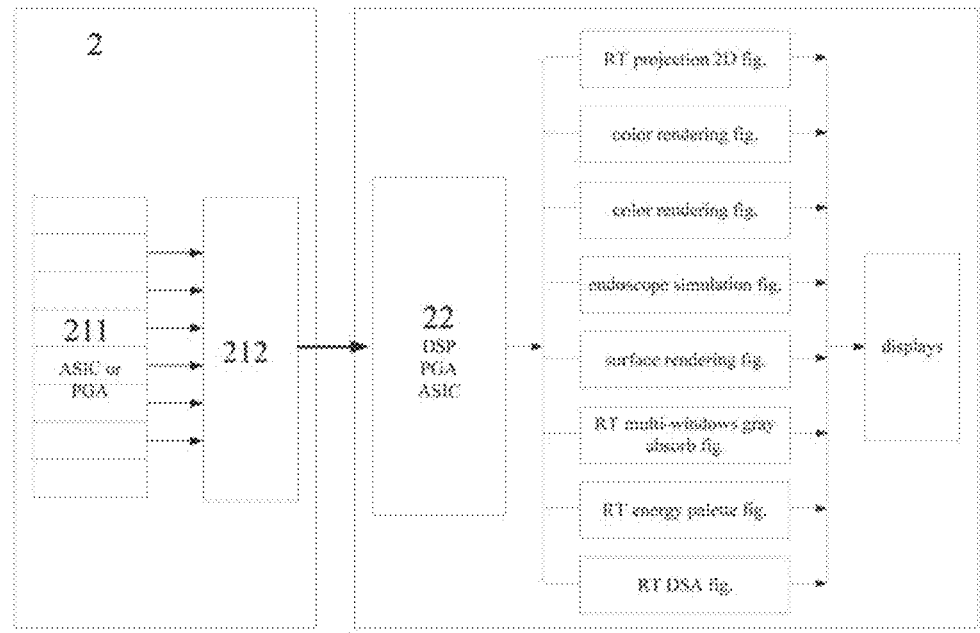
FIG. 16 is a data processing diagram of a visual image processor of the present invention.

As shown in FIG. 16, the parallel reconstruction module 211 transmits the voxel data to the visual image processor, and provides various views of data through variety existing visual algorithm to observers, including but not limited to real-time direction two dimension figure, real-time 3D color rendering figure, endoscope simulation figure, surface rendering figure, real-time multi-window gray absorption figure, real-time energy palette figure and real-time DSA (Digital Subtraction Angiography, digital reduction shadow) figure. Generally speaking, the visual images can be provided 25 frames or block per second, and could be theoretically up to 1024 frames or blocks per second (1024 FPS). Thus, it can meet the needs for dynamic image for the human eyes, and improves the possibility of applying the stationary real-time CT imaging system to intervention surgeries.

Figure 17:
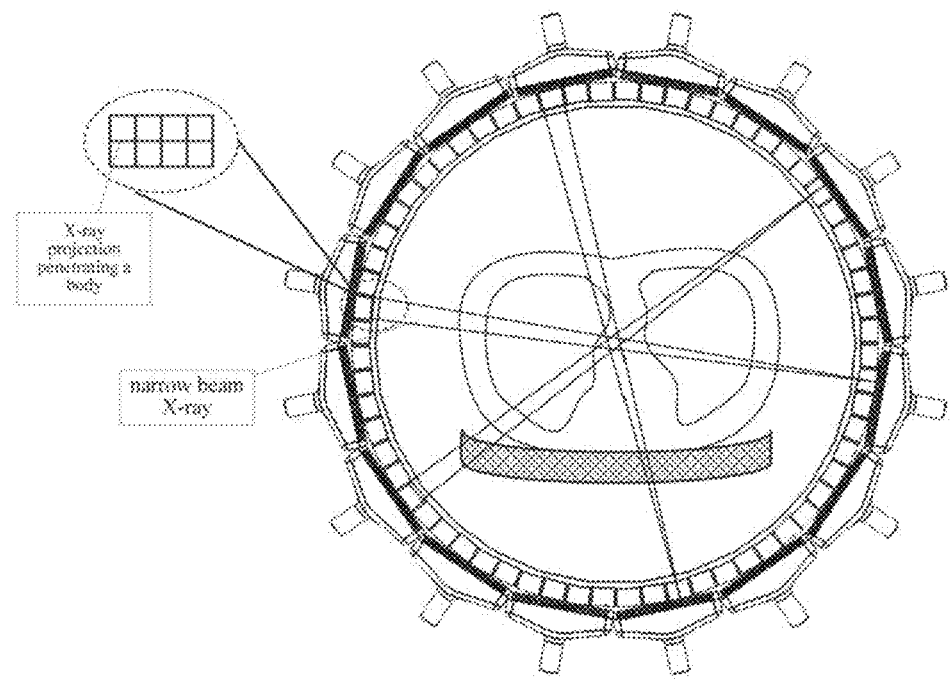
FIG. 17 is a diagram of scan coverage of the pencil beam x-ray in the present invention.

FIG. 17 illustrates the narrow-beam x-rays emitted from several scanning x-ray sources 511 to the photon-counting detector modules 551. The narrow beam x-rays penetrate the body, and direct onto the photon-counting detector modules 551. These direction data can be used to reconstruct the three-dimensional images of the human body.

Figure 18:
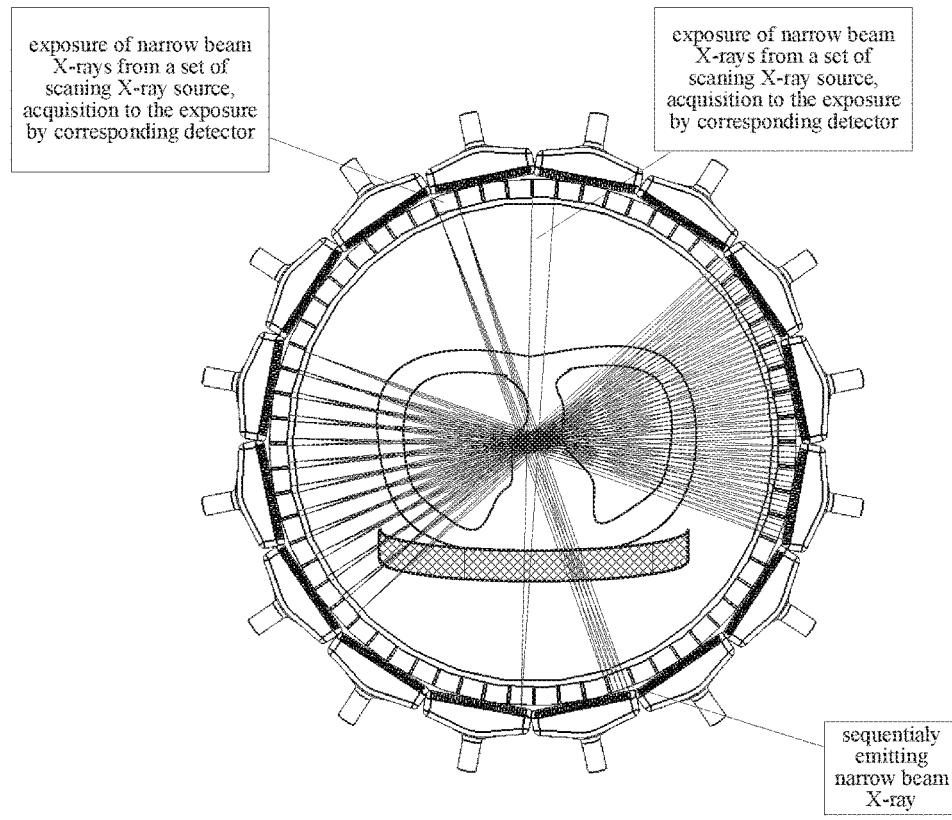
FIG. 18 is a diagram of sequential scan coverage of the pencil beam x-ray in the present invention.

As shown in FIG. 18, a set of scanning x-ray sources 511 sequentially emits narrow beam of x-rays, and the photon-counting detector modules 551 corresponding to the scanning x-ray sources 511 respectively acquire the exposure information. The narrow beam scanning x-rays penetrate the body and direct on the photon-counting detector modules 551 corresponding to the scanning x-ray sources to generate the exposure information. A plurality of narrow beam x-rays could form a group of fan beam x-ray completely covering the body. Under the control of the scan timing controller 41, each narrow beam x-ray could emit sequentially. This mode of the narrow beam x-rays' sequential emission can significantly reduce the scattering effect on imaging and improve the signal to noise ratio and high frequency spatial resolution, compared with the traditional fan beam CT imaging system.

The scan timing controller 41 can control the photon-counting detectors 55 at different spatial positions and the corresponding narrow-beam x-ray sources work in various sequences, so that a variety of beam direction process, a high-speed narrow beam rotation mode, high-speed fan beam rotation mode, divisional parallel rotation modes, as well as other non-rotation scan timing control mode. These different scan timing control modes can assist the stationary real-time CT imaging system 100 to realize complex modes of high speed scan, high precision scan, low-scattering scan or other scan modes.

Disclosed in Chinese patent application document No. 200910022100.3, an x-ray scatter distribution can be taken as the normal distribution. For the one-dimensional case, a narrow beam x-ray passes through an object and directs in X direction, causes x-ray (including direct line and scattering x-rays) intensity distribution as the following equation (1):

$$f(x) = \frac{1}{\sqrt{2\pi}\,\sigma} \exp\left(-\frac{(x-\mu)^2}{2\sigma^2}\right) \quad (1)$$

Where σ represents the object direction characteristic, and its size is determined by the density and thickness; u represents location of the narrow beam x-rays in the x direction.

Figure 19:
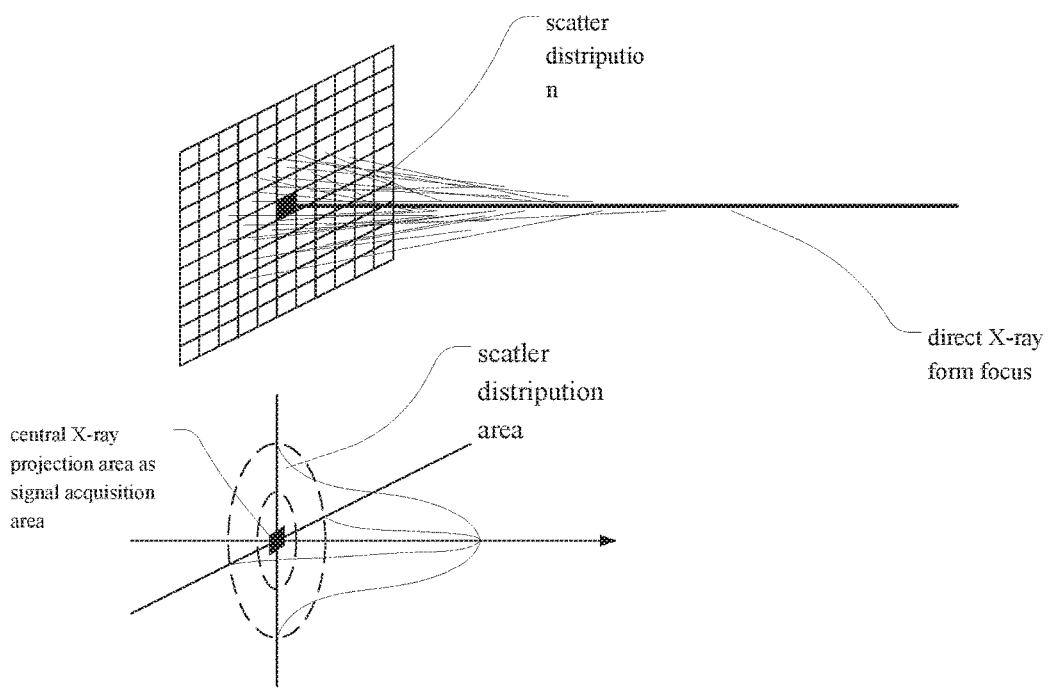
FIG. 19 is a diagram showing the relation between x-ray beam direction area and the scatter distribution.

Referring to FIG. 19, in the condition that a direct x-ray directs from the focus to the corresponding photon-counting detector module, scatter occurs and forms scatter distribution figure. In the figure, black blocks in the center represents central x-ray direction area, taken as the signal acquisition area for acquiring direct x-ray from the focus; circles surrounding the center represents scatter distribution area in which the scatters are mainly distributed. In order to ensure the quality of image acquisition, the scatter should be processed.

By means of controlling work timing of the scan x-ray sources 51 and the photon counting detectors 55, using the scan x-ray sources scanning sequentially and the photon counting detectors capable to control acquisition location, it is ensured that an x-ray expose on only one enough small area at each moment meanwhile only pixels of the photon counting detector in this area are ready to data acquisition. Simultaneously, pixels of the photon counting detectors 55 not in this small area do not work. In this way, scattering contribution to the effective acquisition area will be greatly reduced. In theory, when x-ray directs to a single pixel and only this single pixel is ready to data acquisition, the scatter contribution would approach zero.

It thus can be well understood that the smaller the acquisition area is, the less the scatter contributes. In condition that only a single pixel or small area is able to acquire the x-ray in one direction at each moment, other areas unable to acquire x-ray, scattering component affecting the able-to-acquire pixels in other directions is almost zero, so signals acquired by the pixels in the acquisition area or a single able-to-acquire pixel come substantially from the direct x-rays.

Based on the above principles, the present invention offers the following 4 types of scan timing control mode and corresponding scan control methods, as shown in FIGS. 20A~20C and FIGS. 21A~21D. In the following detail embodiments, it is hypothesized that there are 4*8 (row*column) alignment holes in single acquisition area of an annular scanning x-ray source, all these 4*8 alignment holes directing to a particular photon-counting detector module. Varied designs of the alignment holes in the scanning x-ray sources could be applied in practice, for example, 64*256 alignment holes for high density narrow beam multi exposure, to achieve higher spatial resolution, unfortunately in cost of speed.

Figure 20A:
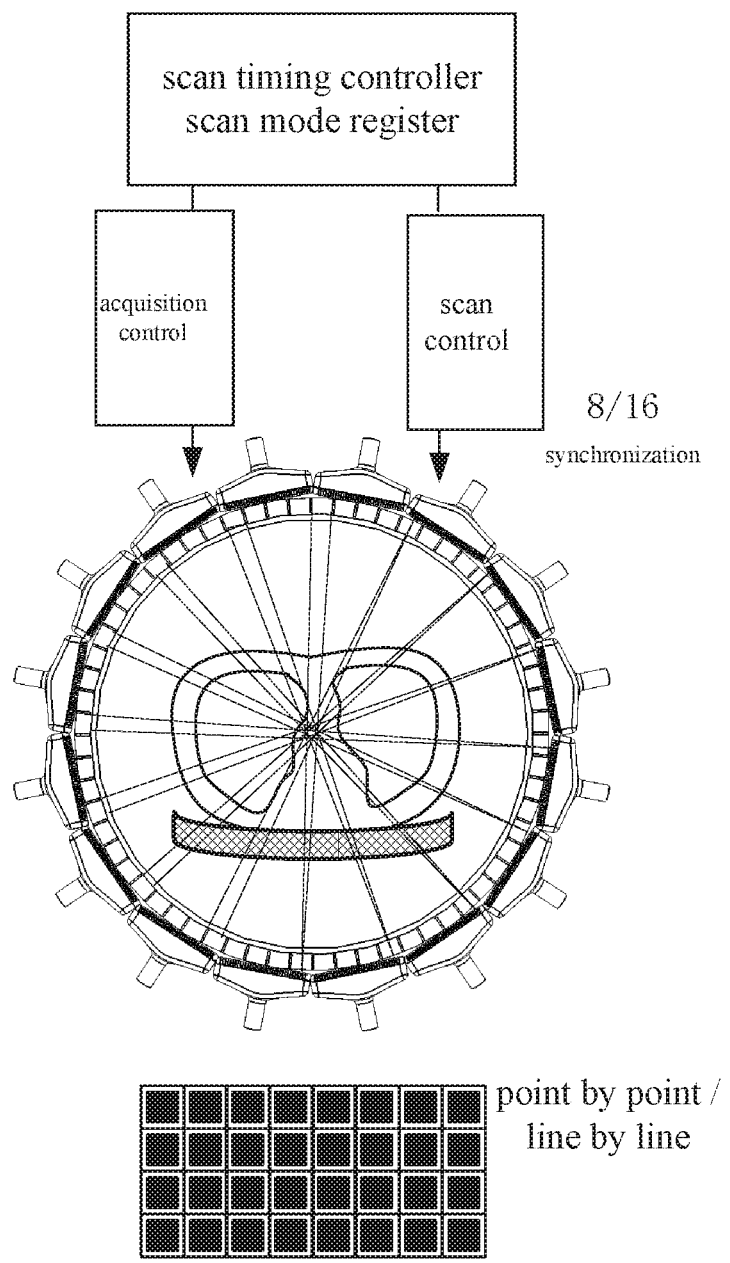
FIGS. 20A, 20B and 20C are diagrams showing timings generated by a scan timing controller of the present invention.

Referring to FIG. 20A, in a first scan timing control mode, the scan x-ray source works in high-speed scan mode. The scan timing controller, cooperating with scan mode register, sequentially control eight scan x-ray sources among 16 scan x-ray sources, each scan x-ray source working in point-by-point and line-by-line mission timing, while control the corresponding photon counting detector pixels acquire the exposure information of the narrow beam x-ray from each alignment hole at each time. The scan results are presented at the bottom half of FIG. 20A. For a scan x-ray source element matrix (64*256 alignment holes) with 256 points in each layer of 64 layers, if scan frequency is 25 KHz (in practice, scan frequency ranges in 10~200 KHz), scan time for each layer is 256*(1/25000)=0.01024 second, and scan speed is 25000/256=97.6 fps (frames per second). That is, exposure and acquisition of narrow beam x-rays in 256 points (256/25000=0.01024) are completed within 0.01024 seconds, and 64 layers in the scan x-ray source element matrix scan within (256*64)/25000=0.65536 seconds. In other words, 64 layers scan in 0.01024*64=0.65536 second. Thus, eight scanning x-ray sources' exposure information are completed in 0.65536 second, the left 8 scanning x-ray sources also need the same amount of time, and scan time for a whole data block is 0.65536*2=1.31072 seconds. The scanning speed of the whole data block is 1/1.31072=0.7629 vps (Volume per second). The data block here refers to a 3D data block, each block consists of a plurality of voxels.

The present scan mode scan in a speed equivalent to that of traditional 64-row fan-beam CT, with a higher signal-to-noise ratio, a lower rotational trail, lower x-ray doses and better image quality. If the present invention uses 4*8 alignment holes, the scan speed could be improved to be 512 times that of 64*256 alignment holes, therefore scanning a full voxel within 1.31072/512=0.00256 seconds and scan 390 voxels per second. Such a scan mode can provide spatial covering density substantially equivalent to that of the 64-row fan-beam CT scanning in a mode of 4 times focus scanning while significantly increases the scanning speed. If the density of detectors is further increased, a higher spatial resolution and the equivalent scan rows can be increased. Due to the narrow-beam x-ray's multiple direction and exposure are equivalent to flying focal spot sampling, 4*8 times flying focal spot resolution can be acquired on 64-row pixels detector module, therefore attaining 256-row scan effect by 64-row 4 times flying focal spot sampling. If scanning x-ray sources with 64*256 alignment holes are applied, it is equivalent to 4096 rows scanning effect by 64 rows 64 times flying focal spot sampling in radius. So, along the circumference, 256 times flying focal spot sampling effects could be achieved, increasing the circumference spatial resolution 256 times.

Figure 20B:
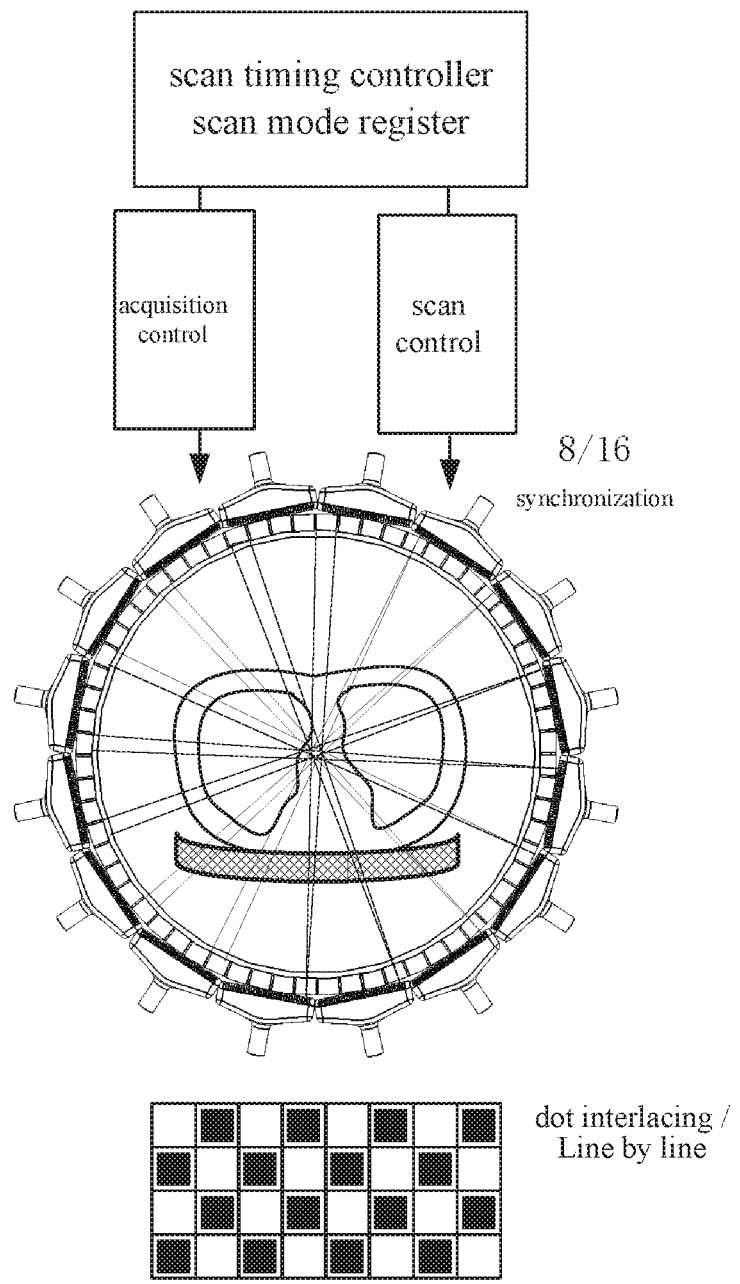

Referring FIG. 20B, in a second scan timing control mode, the scan x-ray source works in high precision scan mode. The scan timing controller 41, cooperating with scan mode registers, sequentially control 16 scan x-ray sources. Each scan x-ray source emits every other point (dot interlacing) and line by line. The scan timing controller 41 also control the corresponding photon counting detector pixels to acquire the exposure information of the narrow beam x-ray by means of acquiring every other point and line by line. That is, the photon counting detector 55 acquires the exposure information of the odd number pixels in a first line and that of the even number pixels in a second line. The scan timing controller 41 controls the timing for the scanning x-ray sources to emit narrow beam x-ray and for the photon counting detectors 55 to acquire, resulting in a scan result presented at the bottom half of FIG. 20B. For a scan x-ray source element matrix with 64-layers, 256 points per layer, scan time for each layer by means of scanning every other point is 128*(1/25000)=0.00512 seconds, scanning speed is 25000/128=195 fps, and scan time for 64 layers is thus (128*64)/25000=0.32768 seconds. By means of 8 of 16 scanning x-ray sources working in parallel, data acquisition of all data blocks takes 0.32768*2=0.65535 seconds.

Similarly, if 4*8 alignment holes are applied in the scanning x-ray source, the scan speed could be increased to 64 times. 4*8 alignment holes can realize 4 times flying focal spot scanning in radius (equivalent to increasing 4 times the pixel density of the detector), and 8 times flying focal spot scanning along circumference (equivalent to increasing 8 times the pixel density of the detector). Thus, 4 times and 8 times the amount of data are respectively achieved.

Figure 20C:
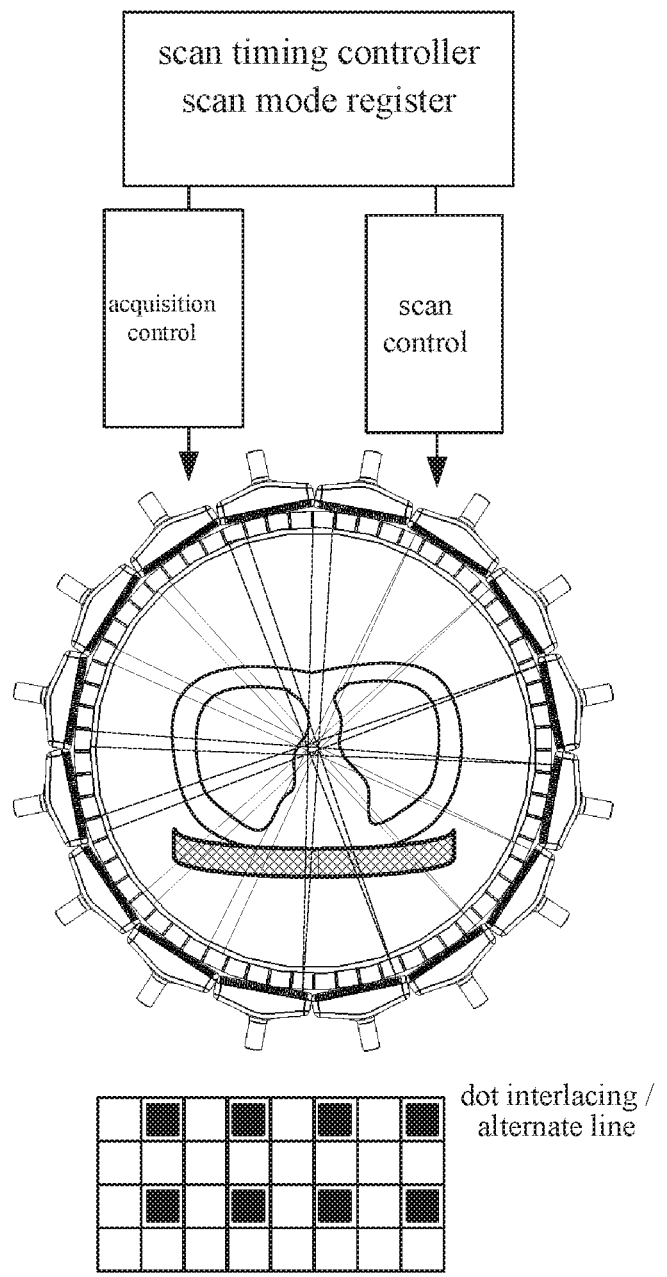

Referring FIG. 20C, in a third scan timing control mode, the scanning x-ray source 511 works in low scattering mode.

The scan timing controller 41, cooperating with scan mode registers, sequentially control 4 of 16 scanning x-ray sources to complete data acquisition of voxels along the circumference in 4 scans. Each scanning x-ray source 511 emits every other point (dot interlacing) and every other line. The scan timing controller 41 also control the corresponding photon counting detector pixels to acquire the exposure information of the narrow beam x-ray by means of acquiring every other point and every other line. That is, the photon counting detector module 551 acquires the exposure information of the odd number pixels in a first line and that of the even number pixels in a second line. The scan timing controller 41 controls the timing for the scanning x-ray sources 511 to emit narrow beam x-ray and for the photon counting detectors module 551 to acquire, resulting in a scan result presented at the bottom half of FIG. 20C. For a scanning x-ray source element matrix with 64-layers, 256 points per layer, scan time for each layer by means of scanning every other point (scan frequency 25 KHz) is $128*(1/25000)=0.00512$ seconds, scanning speed is $25000/128=195$ fps, and scan time for 32 layers (scan every other line) is $(128*32)/25000=0.16384$ seconds. By means of 8 of 16 scanning x-ray sources working in parallel, data acquisition of all voxels takes $0.16384*2=0.32768$ seconds.

Similarly, if 4*8 alignment holes are applied in the scanning x-ray source 511, 4 times flying focal spot scanning in radius, and 8 times flying focal spot scanning along circumference. Thus, 64 times data acquisition is achieved in comparison with above-mentioned scanning x-ray sources with 64*256 alignment holes.

In addition, as shown in FIG. 21A~FIG. 21D, the scanning x-ray sources 511 can realize various scanning modes combination under the control of scan timing controller 41, to meet the needs of different applications. For example, 16 scanning x-ray sources parallelly working in synchronization could be divided into 2 groups of 8 scanning x-ray sources to complete the work in 2 times. Alternatively, they are divided into 4 groups of 4 scanning x-ray sources to complete the work in 4 times. The scan mode could be scanning line by line, every other line or every several lines. The scan mode could be scanning point by point, every other point, or every several points. These different scanning modes combinations enable the present stationary real-time CT imaging system works in different modes, such as fast high-precision mode shown in FIG. 21A, high precision low-scattering model shown in FIG. 21B, low-scattering low precision scanning mode shown in FIG. 21C, fast real-time scanning mode shown in FIG. 21D. In these combinations, when the scanning frequency is 25 KHz (the scanning frequency ranges in 10~200 KHz in practice), different scanning speeds could be achieved, which is not presented herewith.

It is noted that, photon-counting detectors in the embodiment can be replaced with integral detector to perform the same function. The integral detector provides worse imaging effects compared to that provides by the photon-counting detector, but performs relatively stable due to mature integral detector manufacture.

The above-mentioned stationary real-time CT imaging system 100 could be adapted to large field of vision (FOV angle is about 450~500) requirements, by means of the multi-focus annular x-ray sources 511 emitting fan beam x-rays while the x-ray sources and the photon detector modules 551 using non-inverse geometry imaging mode. Details are provided below.

Figure 22:
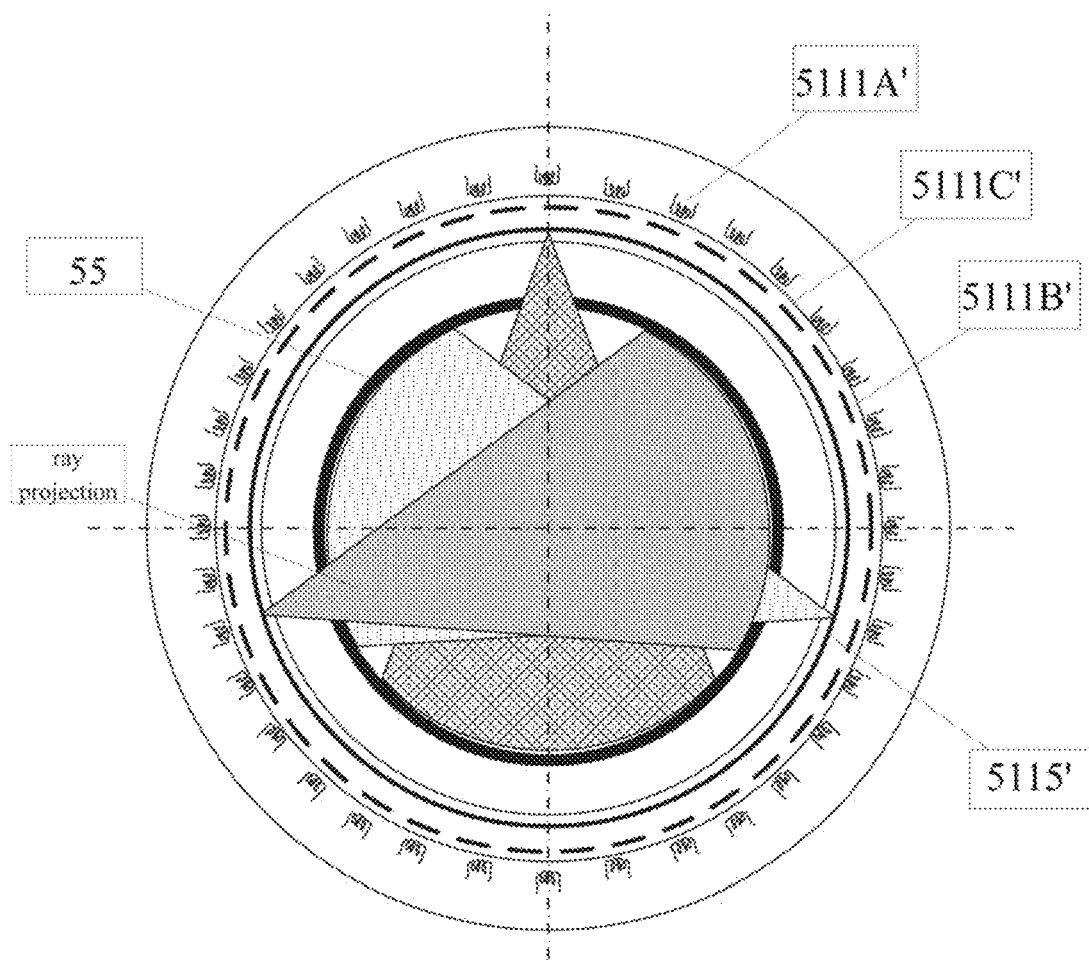
FIG. 22 is a front view of the core portion of the stationary real-time CT imaging system adapted to a large field of vision.
Figure 23:
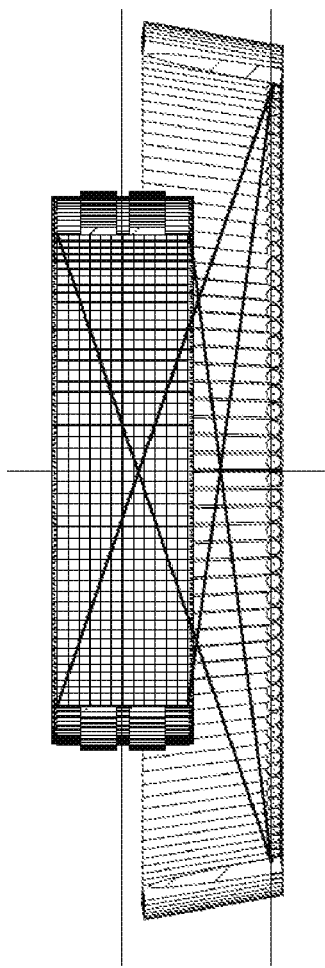
FIG. 23 is a side view of the core portion of the stationary real-time CT imaging system adapted to a large field of vision.

The stationary real-time CT imaging system 100 adapt to the large FOV includes a multi-focus annular x-ray sources 51 and an annular photon detectors 52. The multi-focus annular x-ray sources 51 and annular photon detectors 52 are mounted on rotating bracket along an identical axis, which is Z axis in the CT technology. As shown in FIG. 22, the multi-focus annular x-ray sources emit fan beam x-rays, and the corresponding photon detectors work in an overlap mode. For example, the $1^{st}$ x-ray source works corresponding to the $1^{st}$, $2^{nd}$, $3^{rd}$, $4^{th}$, and $5^{th}$ detectors; the $2^{nd}$ x-ray source corresponding to the $2^{nd}$, $3^{rd}$, $4^{th}$, $5^{th}$ and $6^{th}$ detectors, and so on. The detectors acquire the direction areas along the whole ring of the annular x-ray source, that is, the detectors acquire the direction areas corresponding to a plurality of x-ray source. The focus plane of the multi-focus annular x-ray sources 51 and the central plane in Z direction of the annular photon detector 55 may coincide with each other or not. In view of engineering practice, it is much easier to be implemented that the two planes do not coincide. As shown in FIG. 23, when the two planes do not coincide, x-rays are slanted to the surface of the detector, so necessary geometry correction is required at time of imaging. The specific geometric correction algorithms are well known in this art.

The multi-focus annular x-ray sources 51 may include multiple independent x-ray sources tightly and evenly arrayed in a ring, or a plurality of multi-focus annular x-ray sources with distributed cathodes. Alternatively, the multi-focus x-ray sources 511 may include a plurality of arc x-ray source with evenly distributed cathodes. Preferably, the annular photon detector includes a plurality of photon-counting detectors 551 closely and evenly arrayed in a ring. The x-ray sources 511 arranged along a circumference of the annular photon detector and the photon-counting detectors 551 may be consistent or inconsistent on quantity. As mentioned above, the photon-counting detectors 551 forming the annular photon detector 55 can be replaced by direct conversion x-ray detector, energies distinction x-ray detector or a scintillator-based integral x-ray detector.

Figure 24:
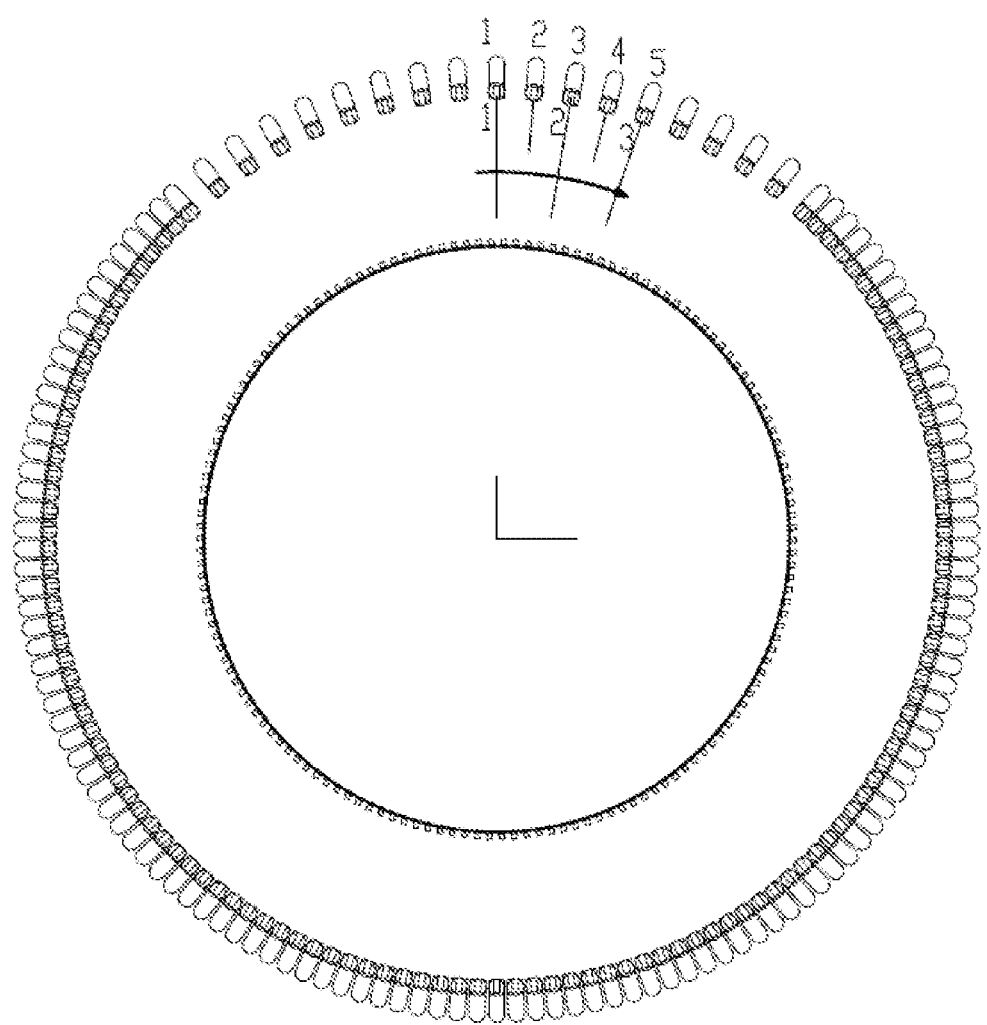
FIG. 24 is a schematic diagram of the multi-focus annular x-ray sources sequentially emitting X-rays and spaced-apart X-rays.
Figure 25:
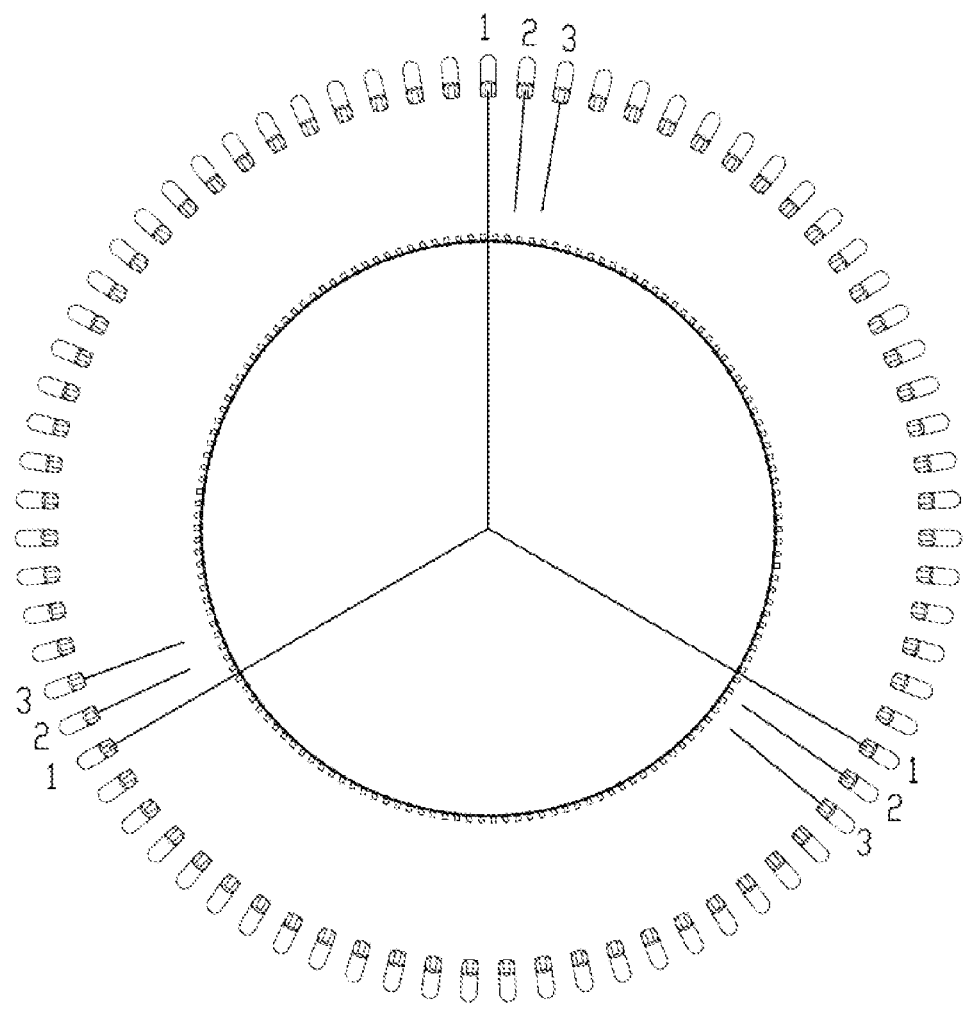
FIG. 25 is a schematic diagram of the multi-focus annular x-ray sources for parallel scanning.

When the stationary real-time CT imaging system 100 works, the multi-focus x-ray sources 51 emits fan beam x-rays along the circumference under control of the scan timing controller 41, which has an effect equivalent to the traditional circular rotation of the spiral CT. It is noted that, the x-ray sources 511 of the multi-focus annular x-ray sources 51 can sequentially emit x-rays in a clockwise or counterclockwise order. As shown in FIG. 24, the x-ray sources of the multi-focus annular x-ray sources 551 can sequentially emit x-rays along the circumference, or every several x-ray sources 551 sequentially emit x-rays. As shown in FIG. 25, the multi-focus annular x-ray sources 51 can simultaneously emit x-rays at single x-ray source or simultaneously emit x-rays in parallel at a plurality x-ray sources. The x-rays emitted in parallel should not interfere with each other in the photon counting detector 551, which restricts the x-ray sources emitting x-rays in parallel to a maximum. It is preferable that the x-ray sources emitting x-rays in parallel are evenly distributed along a circumference of the annular x-ray source.

The x-rays from the multi-focus annular x-ray sources 51 pass through the objects to the corresponding photon-counting detector 551. The data acquisition module 5512 includes a plurality of distributed subsystem (for example, the detector acquisition circuit) that integrated with embedded GPU. The photon-counting detector 551 receives the x-rays and sends the x-rays information to the data acquisition module 5512 by which the image reconstruction is implemented. The reconstructed image information is then sent to an image data storage unit and an interface unit, by which image data storage and visual reproduction are completed. Surely, the traditional CT data acquisition and processing methods could also be applied. That is, the data acquisition and processing unit acquires data, and then transfers the data to the image data storage unit for reconstruction and storage.

Figure 26:
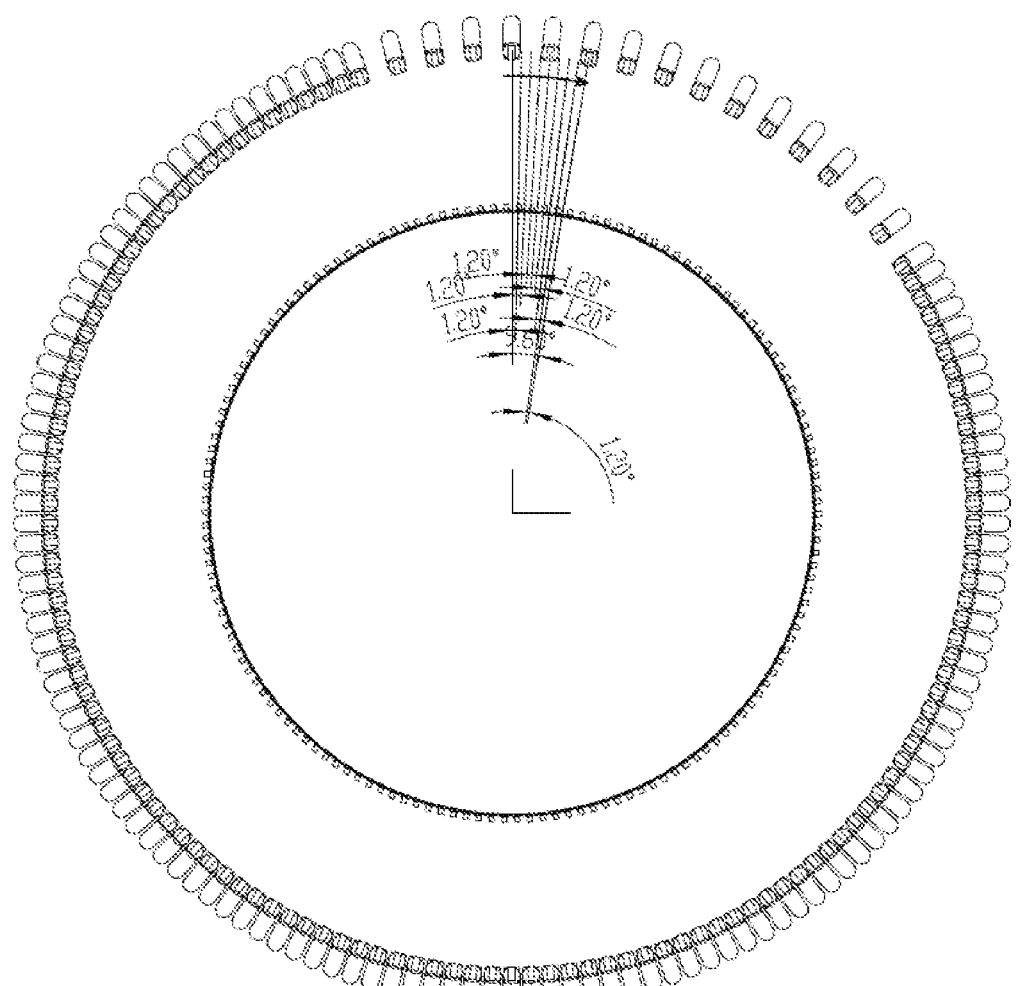
Fig. 26 is a schematic diagram of the multi-focus annular x-ray sources for interpolation scanning.

In the stationary real-time CT imaging system 100, the quantity of the x-ray sources of the multi-focus annular x-ray sources determines circumference maximum direction density at the time of stationary scanning. To meet requirement of some advanced medical technology, the circumference maximum direction density is increased by interpolation scan. As shown in FIG. 26, in condition of interpolation scan, the multi-focus annular x-ray sources 511 evenly rotates an angle which is acquired by dividing 360° by a number of the focus of the multi-focus annular x-ray source, and emits x-rays in several times during the period that the multi-focus annular x-ray sources 51 rotates within the angle range, which is equivalent to add several x-ray sources between the two x-ray sources (x-rays' emission times equal to the quantity of the interpolation of the interpolation scan).

At the time of interpolating scan, it may be the multi-focus annular x-ray sources 511 swing within a small angle along the circumference. Alternatively, the multi-focus annular x-ray sources 51 and the annular photon detectors 55 relatively swing along the circumference. Alternatively, the bed may swing with the body along the circumference without a rotating bracket. Referring to swing interpolation principle shown in FIG. 27, in an embodiment of the present invention, there are 150 focuses evenly distributed along a circumference, adjacent focuses spacing for 26 mm. If the multi-focus annular x-ray sources and the annular photon detector relatively swing 2.4° (360/150=2.4), the direction number increases by the swing interpolation caused by the focus swing within 26 mm, which effectively improves image reconstruction quality.

Figure 27:
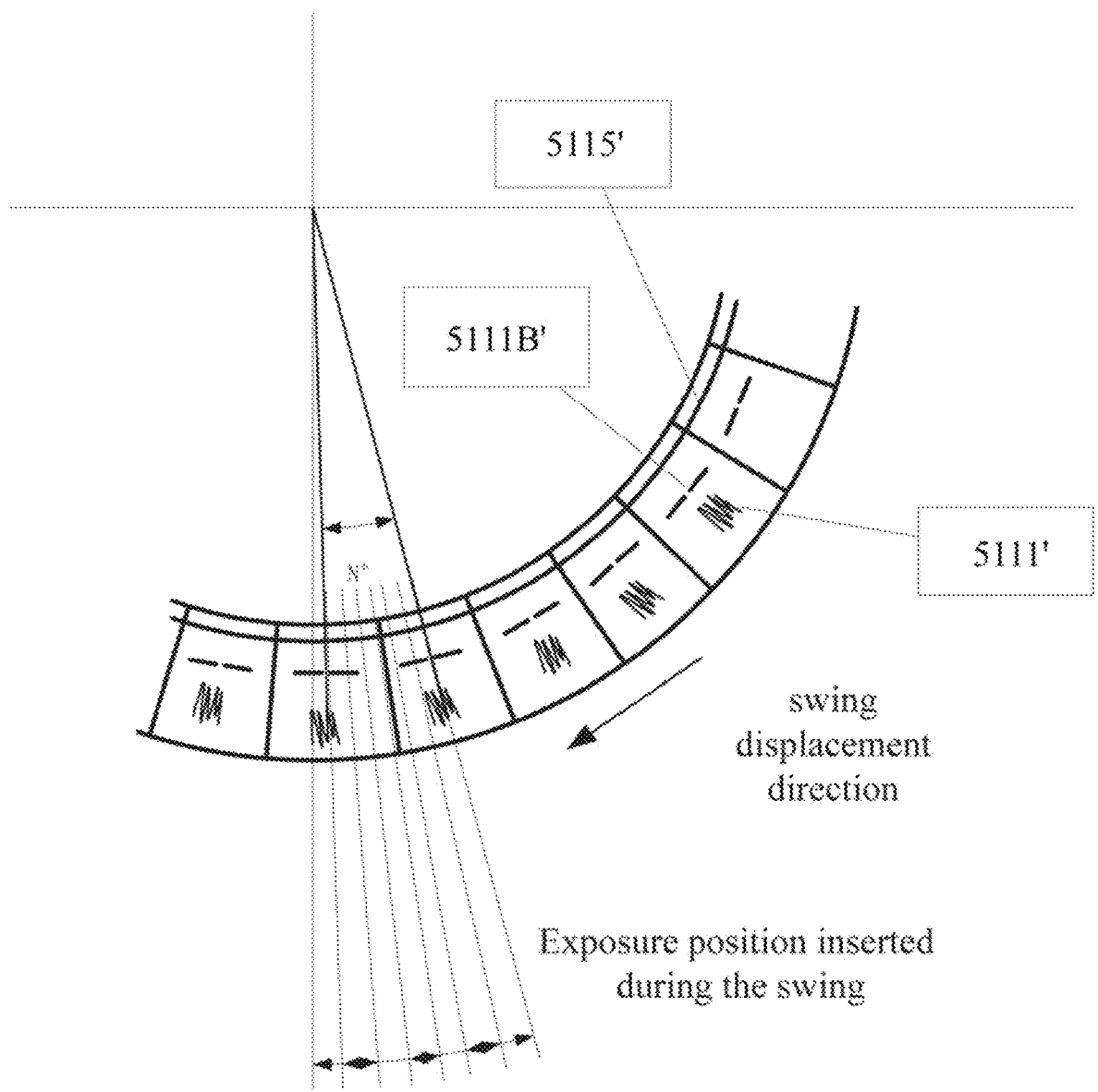
FIG. 27 is a schematic diagram of the multi-focus annular x-ray sources for swing interpolation.
Figure 28:
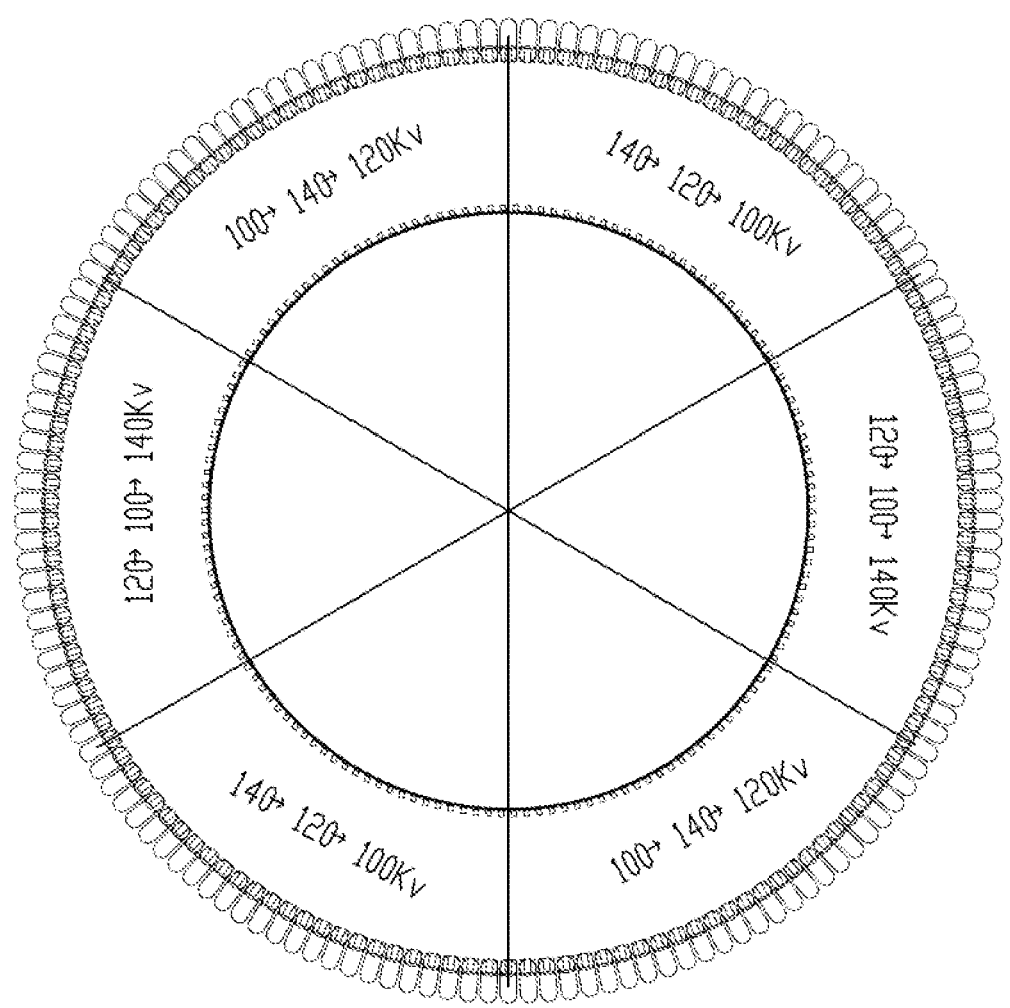
FIG. 28 is a schematic diagram of the multi-focus annular x-ray sources for circular multi-spectral scanning.

As is shown in FIG. 28, the stationary real-time CT imaging system 100 can implement a variety of energy spectrum scan by multi-focus annular x-ray sources 51. Firstly, the multi-focus annular x-ray sources 511 can implement energy spectrum scan using single scan x-ray source's energy instantaneous switching to instantaneously switch energy levels (for example, FIG. 27 showing the switch among 100 kV, 120 kV, and 140 kV). Specific quantity of the energy levels for switching is determined by design needs. A scanning x-ray source completes an energy spectrum scan by means of energy instantaneous switching, and next scanning x-ray source sequentially completes energy spectrum scan in the same way under control of the scan timing controller 41, until all the scanning x-ray sources 511 complete scan. Secondly, the multi-focus annular x-ray sources 51 may conduct energy spectrum scan using circumferential intermittent energy switch. That is, all the scanning x-ray sources of the multi-focus annular x-ray sources 51 simultaneously complete a circumferential scan under the control of the scan timing controller 41 with the same energy level, then complete another circumferential scan with another energy level, and repeat the scan until all energy levels have been switched. Alternatively, the multi-focus annular x-ray sources 51 may implement energy spectrum scan by circumferential multi-energy-levels-scan. That is, the scanning x-ray sources 511 along the circumference are divided into several groups, the scanning x-ray sources in a same group using an identical energy level and each group's energy level being different from other groups. The scanning x-ray sources 511 complete a circumferential scan under the control of scan timing controller 41, and then each group respectively switch to corresponding another energy level to repeat another circumferential scan, until complete the circumferential scans respectively with all the energy levels.

The present embodiment uses the scanning x-ray sources 51 and the photon-counting detectors 55 arrayed in a ring, without high speed rotary mechanical elements, so that it is completely different from the current widely used CT imaging system. It significantly reduces the manufacturing difficulty, and enhances the accuracy and speed of detecting in the CT imaging system 100. By means of electronically controlling the x-ray beams to sequentially direct on different positions in a stationary scan mode, instead of the traditional rotary scan mode, scan speed could be improved dozens of times to more than 25 circles per second. In combination with the high speed real time reconstruction system, the present invention can reconstruct dynamic three-dimensional images, avoiding considerable inertia of the traditional high speed machinery rotary scan mode. Because up to 25 blocks per second can be real-time reconstructed, the application of the present CT imaging system 100 in the intervention operation becomes possible. In addition, the narrow-beam x-ray directs onto a smaller area on the photon-counting detector, bring advantages that the scatter interferes signals less and signal to noise ratio is increased at less doses.

To sum up, a stationary real-time CT imaging system 100 in the present invention achieves better images in real time at radiation doses that is one-tenth of the radiation doses for traditional CT imaging system 100, which make patients suffer radiation doses less than safe requirement for more accurate diagnosis.

The stationary real-time CT imaging system 100 and imaging control method are explained in detail. As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A stationary real-time CT imaging system, including a bed control unit, a CT host and interface unit, a power control unit, a main processor, and a scan host, wherein:
   the scan host includes an annular scanning x-ray source and an annular photon-counting detector, said annular scanning x-ray source and said annular photon counting detector being in different planes parallel to each other;
   the annular scanning x-ray source includes a plurality of scanning x-ray sources closely arrayed in a ring, and the annular photon-counting detector includes a plurality of photon-counting detector modules closely arrayed in a ring;
   the scanning x-ray source is configured to sequentially emit pencil beam x-rays to corresponding photon counting detector module, the x-rays penetrating through an object, wherein the photon counting detector modules send corresponding exposure information, via the scan host and the main processor, to the CT host and interface unit, and the CT host and interface unit completes reconstruction and visual reproduction of an image in real time,
   wherein the pencil beam x-ray exposes on an area at each moment while only pixels of the photon counting detector in the area are ready to acquire the exposure information and pixels of the photon counting detectors not in the area do not work.

2. The stationary real-time CT imaging system according to claim 1 wherein the main processor has a scan timing controller, which controls a plurality of scanning x-ray sources that locate in different areas to work simultaneously or sequentially.

3. The stationary real-time CT imaging system according to claim 1 wherein each photon-counting detector module includes an independent data acquisition module and a data transmission channel for data transmission in GHz or THz frequencies.

4. The stationary real-time CT imaging system according to claim 1 wherein:
the scan host further includes a photon-counting detector controller, a multi-channel photon-counting detector acquisition circuit, multi-channel data transmission channels and a data preprocessor;
each photon-counting detector module is configured to complete initial integration of acquired data and to send the integrated data to the multi-channel photon-counting detector acquisition circuit, wherein the multi-channel data transmission channels are configured to receive the data from the multi-channel photon-counting detector acquisition circuit and then send the received data to the data preprocessor.

5. The stationary real-time CT imaging system according to claim 1 wherein:
the CT host and interface unit includes a real time reconstruction system and main control computer that connects with a multi-mode scan timing generator in the main processor;
the multi-mode scan timing generator connects with a scan timing controller and the photon-counting detector controller.

6. The stationary real-time CT imaging system according to claim 4 wherein:
the data preprocessor is configured to process the data from the multi-channel data transmission channels, into data frames, and then transmit the data frames to the high speed data transmission channel and
the real-time reconstruction systems and main control computer.

7. A stationary real-time CT imaging system, including a bed control unit, a CT host and interface unit, a power control unit, a main processor, and a scan host, wherein:
the scan host includes a multi-focus annular scanning x-ray sources and an annular photon-counting detector;
the multi-focus annular x-ray sources includes a plurality of scanning x-ray sources closely arrayed in a ring, and the annular photon-counting detector includes a plurality of photon-counting detector modules closely arrayed in a ring;
each scanning x-ray source sequentially emits fan beam ray x-rays directing to a corresponding photon counting detector module, the x-rays having penetrated through an object, the photon counting detector modules work in overlap mode and send corresponding exposure information, via the scan host and the main processor, to the CT host and interface unit, the CT host and interface unit completes reconstruction and visual reproduction of an image in real time,
wherein the pencil beam x-ray exposes on an area at each moment while only pixels of the photon counting detector in the area are ready to acquire the exposure information and pixels of the photon counting detectors not in the area do not work.

8. The stationary real-time CT imaging system according to claim 7 wherein:
the multi-focus annular x-ray source is configured to evenly rotates an angle which is acquired by dividing 360° by a number of the focuses of the multi-focus annular x-ray source, and to emit the pencil beam x-rays in several times during the period that the multi-focus annular x-ray sources rotates by the angle.

9. The stationary real-time CT imaging system according to claim 7 wherein
the scanning x-ray sources of the multi-focus annular x-ray source are configured to completes energy spectrum scans by means of energy instantaneous switching in turns, until all the scanning x-ray sources complete the energy spectrum scans,
wherein, in the energy spectrum scan, single scan x-ray source instantaneously switches multiple energy levels.

10. The stationary real-time CT imaging system according to claim 7 wherein:
all the scanning x-ray sources of the multi-focus annular x-ray source simultaneously complete a circumferential scan under the control of the scan timing controller with the same energy level, then complete another circumferential scan with another energy level.

11. The stationary real-time CT imaging system according to claim 10 wherein:
the scanning x-ray sources distributed along a circumference of the annual x-ray source are divided into several groups, the scanning x-ray sources in a same group using an identical energy level and each group's energy level being different from that of other groups.

* * * * *